(12) United States Patent
Bloom

(10) Patent No.: US 9,131,980 B2
(45) Date of Patent: Sep. 15, 2015

(54) ELECTROSURGICAL DEVICES

(75) Inventor: Eliot F. Bloom, Hopkinton, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 760 days.

(21) Appl. No.: 13/330,132

(22) Filed: Dec. 19, 2011

(65) Prior Publication Data

US 2013/0158536 A1    Jun. 20, 2013

(51) Int. Cl.
*A61B 18/14* (2006.01)
*A61B 18/00* (2006.01)

(52) U.S. Cl.
CPC ..... *A61B 18/1492* (2013.01); *A61B 2018/0016* (2013.01); *A61B 2018/0022* (2013.01); *A61B 2018/00023* (2013.01); *A61B 2018/00029* (2013.01); *A61B 2018/00267* (2013.01); *A61B 2018/00404* (2013.01); *A61B 2018/00434* (2013.01); *A61B 2018/00494* (2013.01); *A61B 2018/00511* (2013.01); *A61B 2018/00541* (2013.01); *A61B 2018/00589* (2013.01); *A61B 2018/1435* (2013.01); *A61B 2018/1437* (2013.01); *A61B 2018/1465* (2013.01); *A61B 2018/1472* (2013.01); *A61B 2218/002* (2013.01)

(58) Field of Classification Search
CPC ............ A61B 18/1492; A61B 2218/002; A61B 2018/0016; A61B 2018/00214; A61B 2018/0022; A61B 2018/00267; A61B 2018/1437; A61B 2018/1465; A61B 2018/1467; A61B 2018/1472
USPC .......................................................... 606/41
See application file for complete search history.

(56) References Cited

U.S. PATENT DOCUMENTS

| | | | |
|---|---|---|---|
| 4,060,088 A | 11/1977 | Morrison, Jr. et al. | |
| 4,195,637 A | 4/1980 | Gruntzig et al. | |
| 5,169,386 A | 12/1992 | Becker et al. | |
| 5,496,271 A | 3/1996 | Burton et al. | |
| 5,713,942 A | 2/1998 | Stern et al. | |
| 5,751,729 A | 5/1998 | Aybay | |
| 6,004,269 A | 12/1999 | Crowley et al. | |
| 6,036,689 A * | 3/2000 | Tu et al. ........................ | 606/41 |
| 6,216,704 B1 | 4/2001 | Ingle et al. | |
| 6,558,385 B1 | 5/2003 | McClurken et al. | |
| 6,623,515 B2 * | 9/2003 | Mulier et al. ................. | 607/105 |
| 6,656,174 B1 | 12/2003 | Hegde et al. | |
| 6,689,131 B2 | 2/2004 | McClurken | |
| 6,702,810 B2 | 3/2004 | McClurken et al. | |
| 6,953,461 B2 | 10/2005 | McClurken et al. | |

(Continued)

FOREIGN PATENT DOCUMENTS

WO    WO 2010/078875    7/2010

OTHER PUBLICATIONS

Salameh, F., et al., "An animal model study to clarify and investigate endoscopic tissue coagulation by using a new monopolar device," *Gastrointestinal Endoscopy* 59:107-112, American Society for Gastrointestinal Endoscopy (2004).

*Primary Examiner* — Michael Kahelin
*Assistant Examiner* — Mallika D Fairchild
(74) *Attorney, Agent, or Firm* — Jeffrey J. Hohenshell

(57) ABSTRACT

An electrosurgical device includes a tubular shaft defining a shaft lumen, and a tubular electrode defining an electrode lumen, the electrode being coupled to the shaft. In a straight configuration, the electrode is configured to retain fluid within the electrode lumen, and, in a bent configuration, the electrode is configured to release fluid from within the electrode lumen to an exterior of the electrode.

12 Claims, 17 Drawing Sheets

(56) References Cited

U.S. PATENT DOCUMENTS

| | | |
|---|---|---|
| 7,537,595 B2 | 5/2009 | McClurken |
| 7,604,635 B2 | 10/2009 | Mcclurken et al. |
| 7,608,072 B2 | 10/2009 | Swanson |
| 7,645,277 B2 | 1/2010 | McClurken et al. |
| 7,651,494 B2 | 1/2010 | McClurken et al. |
| 7,691,050 B2 | 4/2010 | Gellman et al. |
| 7,736,361 B2 | 6/2010 | Palanker |
| 7,811,282 B2 | 10/2010 | McClurken |
| 7,815,634 B2 | 10/2010 | McClurken et al. |
| 7,909,820 B2 | 3/2011 | Lipson |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,038,670 B2 | 10/2011 | McClurken |
| 8,048,070 B2 | 11/2011 | O'Brien et al. |
| 8,083,736 B2 | 12/2011 | McClurken |
| 8,177,783 B2 | 5/2012 | Davison et al. |
| 8,475,455 B2 | 7/2013 | McClurken |
| 2002/0082634 A1 | 6/2002 | Kammerer et al. |
| 2003/0144656 A1 | 7/2003 | Ocel |
| 2003/0216724 A1 | 11/2003 | Jahns |
| 2004/0049179 A1 | 3/2004 | Francischelli |
| 2004/0087940 A1 | 5/2004 | Jahns |
| 2004/0138621 A1 | 7/2004 | Jahns |
| 2004/0267326 A1 | 12/2004 | Ocel |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0165392 A1 | 7/2005 | Francischelli |
| 2005/0171525 A1 | 8/2005 | Rioux et al. |
| 2005/0209564 A1 | 9/2005 | Bonner |
| 2006/0106375 A1 | 5/2006 | Werneth et al. |
| 2008/0262489 A1 | 10/2008 | Steinke |
| 2009/0177192 A1 | 7/2009 | Rioux et al. |
| 2009/0270856 A1 | 10/2009 | Saadat et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2010/0312259 A1 | 12/2010 | Houser et al. |
| 2011/0137298 A1 | 6/2011 | Nguyen et al. |
| 2011/0178515 A1 | 7/2011 | Bloom et al. |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0184983 A1 | 7/2012 | Chang et al. |
| 2012/0253343 A1 | 10/2012 | McClurken et al. |
| 2013/0085493 A1 | 4/2013 | Bloom et al. |

* cited by examiner

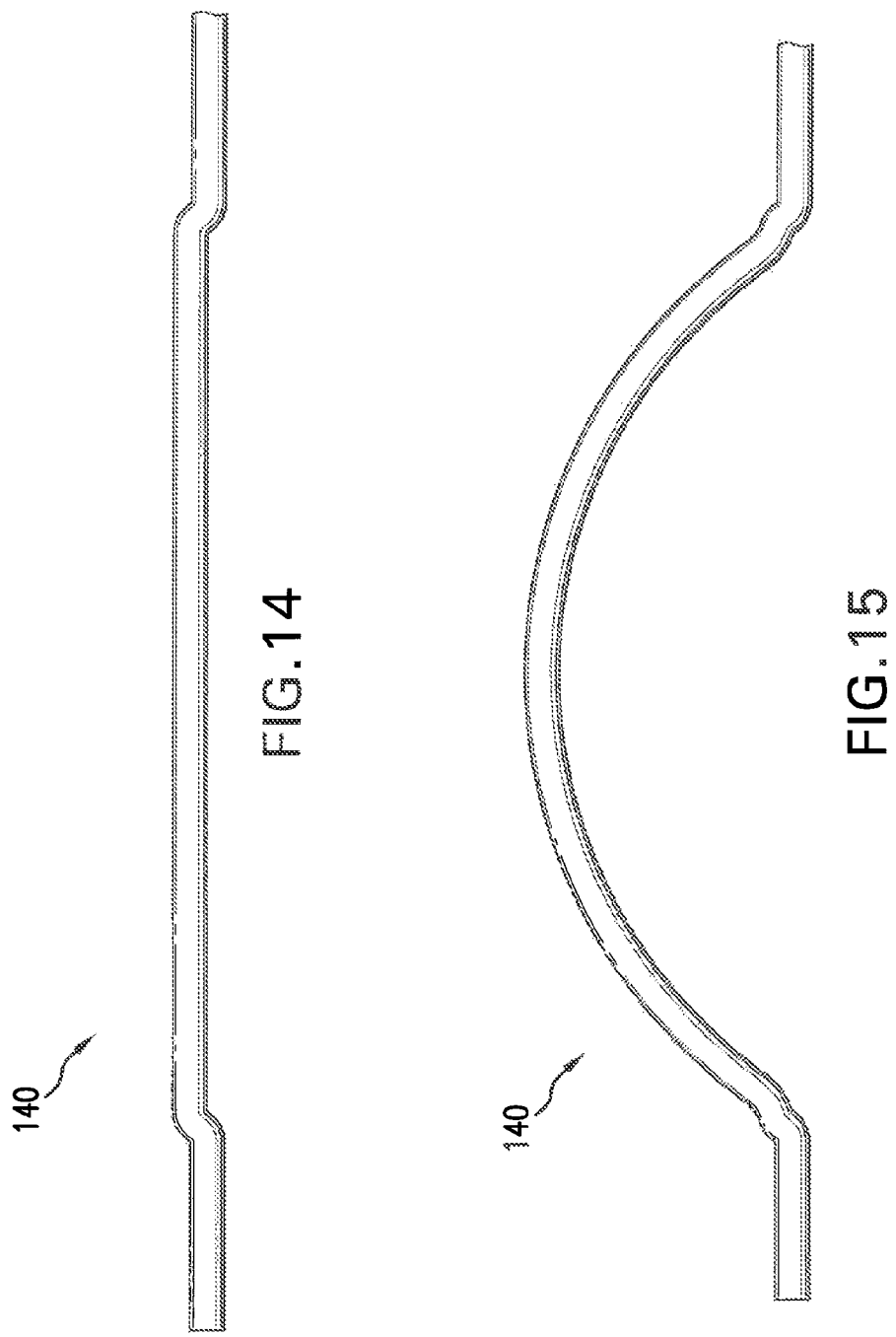

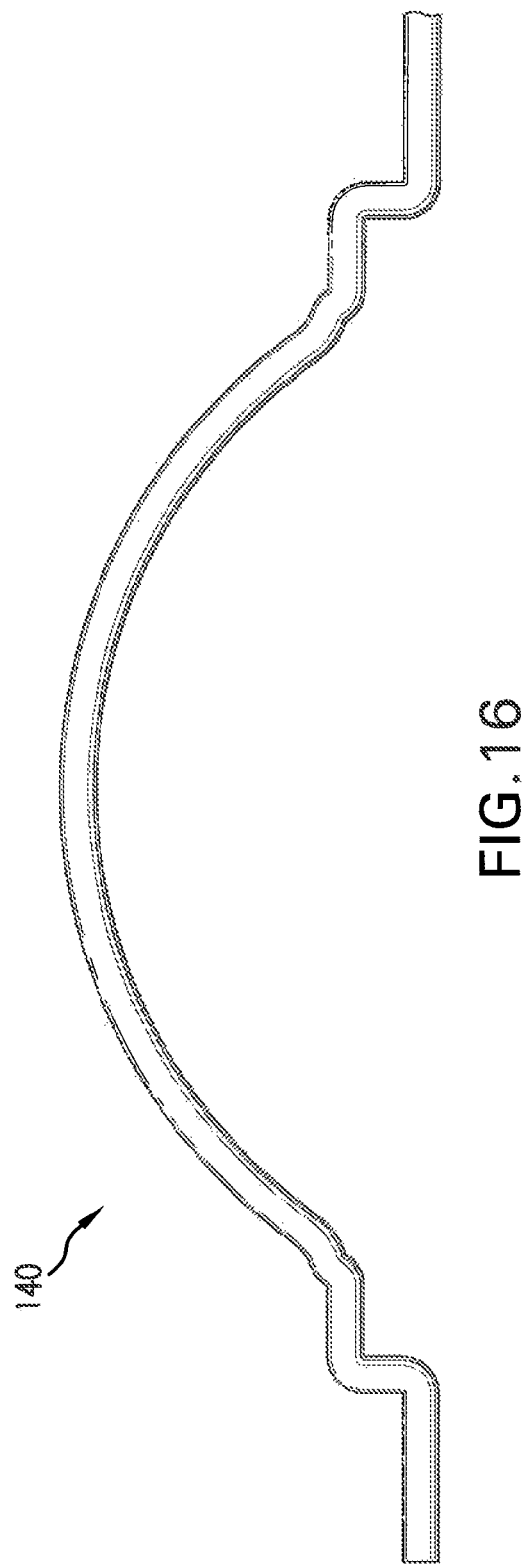

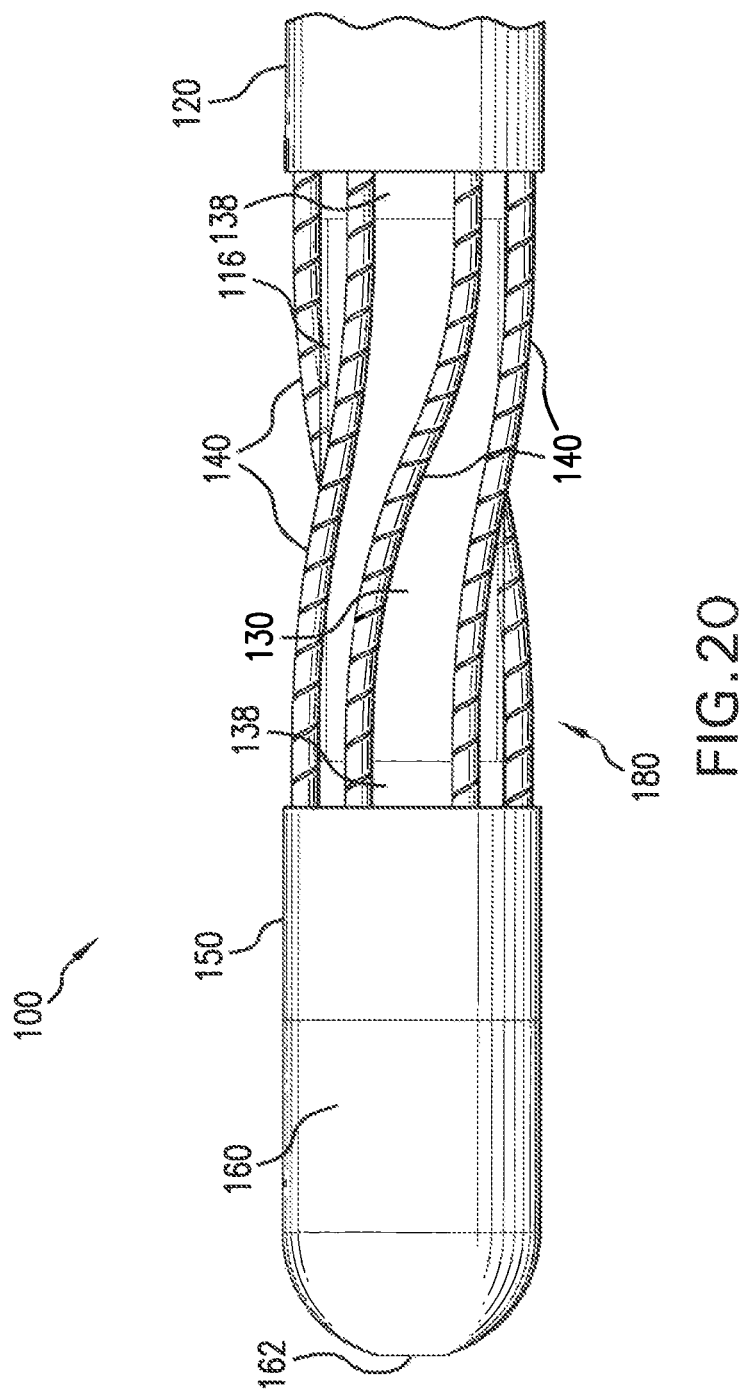

ELECTROSURGICAL DEVICES

BACKGROUND OF THE INVENTION

1. Field of the Invention

The present invention relates to medical devices, particularly to an electrosurgical device having one or more electrodes defining central axial lumens, where the electrodes are configured to release saline from their lumens.

2. Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a target location. It is sometimes desirable to perform electrosurgical procedures at the target location.

An electrosurgical procedure involves a medical device having an electrode tip that is electrically energized to perform a procedure such as coagulation, dissection, desiccation, cautery, and hemostasis (including hemostatic sealing and coagulation of soft tissue and/or bone at a surgical site). The electrical energy can be provided in either direct current (DC) form or in alternating current (AC) form. Low frequency electrical energy, including DC, can stimulate muscle and nerves and have potentially undesirable outcomes, such as cardiac arrest, if not properly handled. Higher frequency electrical energy, and in particular electrical energy in the radiofrequency (RF) range (e.g., about 3 kilohertz to about 300 gigahertz), may not stimulate muscle or nerves, and therefore may be better suited to core and coagulate tissue. An electrode tip energized by ultrasonic energy can also be used to perform electrosurgical procedures such as coagulation and tissue ablation.

Modern day elongated medical devices can provide percutaneous access to inner organs and other tissue, and can allow clinicians to navigate to remote and narrow locations within a body. To provide such percutaneous access, these elongated medical devices must meet a variety of requirements such as a desired length, a sufficiently small outer diameter to permit navigation through narrow body passageways, and sufficiently large inner diameter to permit direct delivery of the required functionality to the remote location. In the case of an elongated medical device having an RF-powered electrode tip, for example, the device can have an inner diameter sufficiently large to transfer the required energy to the electrode tip. To guide the electrode tip to the target site within a body, the elongated medical device including the electrode tip can be deployed into the body through a small trocar. The elongated medical device can be advanced in the body to the target site in the body, and the electrode tip can be energized at the target site to perform the electrosurgical procedure. An elongated delivery system (e.g., a delivery catheter and/or guidewire) can be used to guide the elongated medical device through the body to the target site.

Electrode tips delivering RF energy can be monopolar or bipolar. A monopolar tip includes one electrode, and a ground pad electrode is located on the patient. Energy applied through the electrode travels through the patient to ground, typically the ground pad. With a bipolar tip, the ground pad electrode located on the patient is eliminated and replaced with a second electrode pole as part of the tip. These active and return electrodes of a bipolar tip are typically positioned close together to ensure that, upon application of electrical energy, current flows directly from the active to the return electrode. Bipolar tips can be advantageous compared to monopolar tips because the return current path only minimally flows through the patient. In bipolar tips, portions of both the active and return electrode are typically exposed so they may both contact tissue, thereby providing a current path from the active to the return electrode through the tissue. Also, the depth of tissue penetration may be advantageously less with a bipolar tip than with a monopolar tip.

BRIEF SUMMARY

What is needed is an electrosurgical device having the ability to selectively apply working fluid and electrosurgical energy to target tissue from one or more electrodes. The present invention satisfies the above needs and provides further related advantages as will be made apparent by the description of the embodiments that follow.

Electrodes and electrosurgical devices using such electrodes are presented. In some embodiments, an electrosurgical device includes a tubular electrode coupled to a tubular shaft. The electrode is configured to retain fluid within an axial lumen thereof when in a straight configuration, and is configured to release fluid from within its axial lumen when in a bent configuration.

In some embodiments, an electrode for an electrosurgical device includes an elongated tubular wall defining a central axial lumen. The electrode is configured to retain fluid within an axial lumen thereof when in a straight configuration, and is configured to release fluid from within its axial lumen through its wall when in a bent configuration.

Methods of using the electrodes and electrosurgical devices to treat tissue are also presented.

BRIEF DESCRIPTION OF THE FIGURES

The accompanying drawings, which are incorporated herein and form a part of the specification, illustrate the present invention and, together with the description, further serve to explain the principles of the invention and to enable a person skilled in the pertinent art to make and use the invention. In the drawings, like reference numbers, letters, or renderings indicate identical or functionally similar elements.

FIG. 14 illustrates a side view of an electrode of the electrosurgical device of FIG. 1 in a straight configuration, according to an embodiment presented herein.

FIG. 15 illustrates a side view of an electrode of the electrosurgical device of FIG. 1 in a bent configuration, according to an embodiment presented herein.

FIG. 16 illustrates a side view of an electrode of the electrosurgical device of FIG. 1 in a bent configuration, according to an embodiment presented herein.

FIG. 20 illustrates a partial side view of an electrosurgical device with a plurality of electrodes according to an embodiment presented herein.

DETAILED DESCRIPTION OF THE INVENTION

Figure 1:
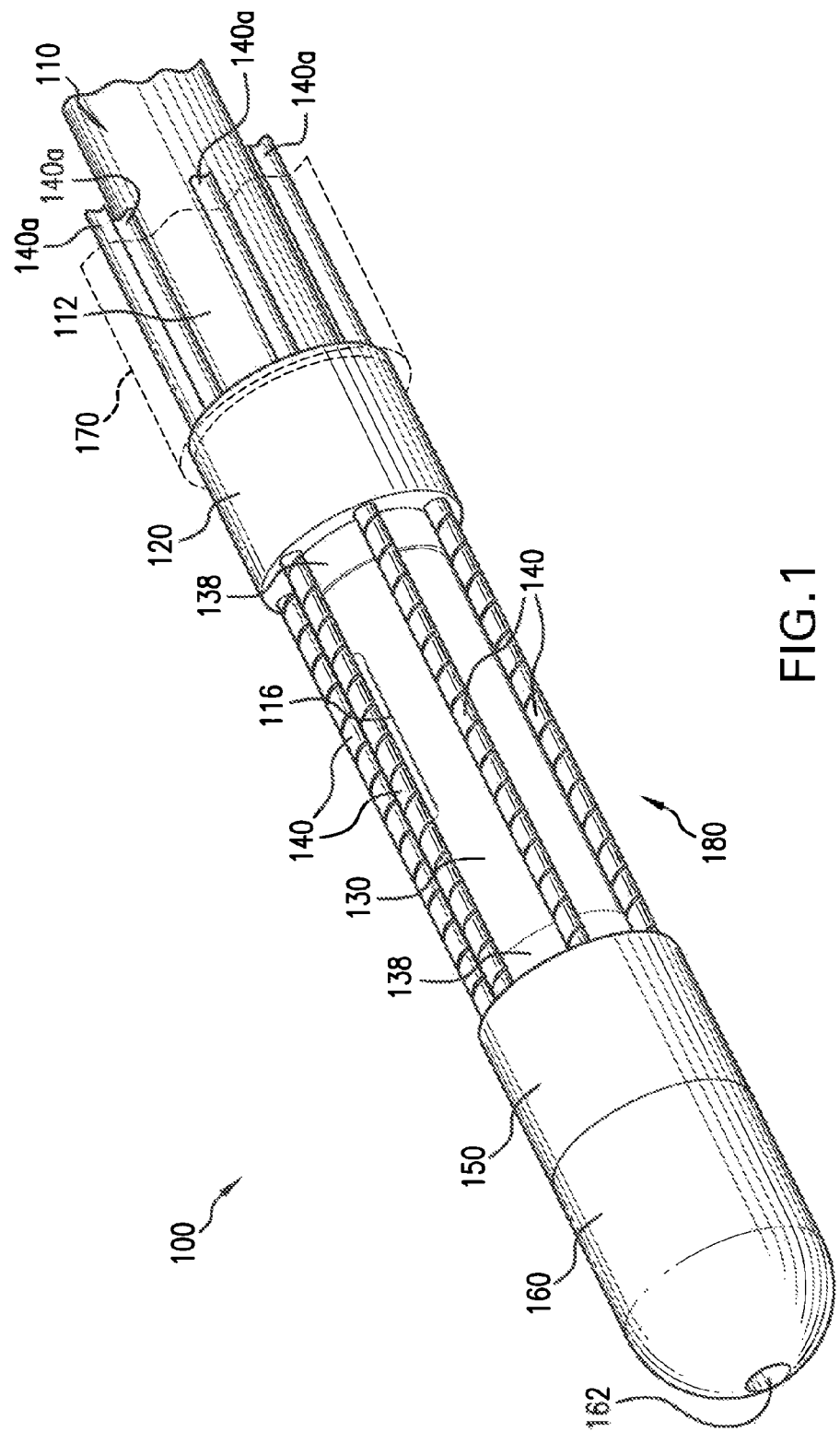
FIG. 1 illustrates a perspective view of an electrosurgical device in a straight configuration, according to an embodiment presented herein.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

The term "invention" or "present invention" as used herein is a non-limiting term and is not intended to refer to any single embodiment of the particular invention but encompasses all possible embodiments.

According to some embodiments of the present invention, an electrosurgical device includes one or more electrodes external to and positioned about an expandable balloon (i.e., a balloon that can be expanded by inflation with a gas or liquid). The balloon can be formed of a non-conductive substrate material. The electrosurgical device can be incorporated into a catheter assembly. The balloon can be disposed at a distal end of an elongated medical device (e.g., a catheter) to provide the catheter with electrosurgical functionality. Electrode leads (including proximal extensions of the electrodes) can be connected to a power source at a proximal end of the catheter.

The one or more electrodes can be formed of any suitable material. For example, the electrode(s) can be a biocompatible conductive material (such as, for example, conductive polymer, stainless steel, nitinol, or titanium), or a nonconductive material (such as, for example, a nonconductive polymer) with a conductive coating (such as, for example, conductive paint or conductive ink) applied to at least a portion of its outer surface.

The proximal and distal ends of the balloon can be fixed to an interior shaft (which may be a catheter sheath) of the electrosurgical device by rigid rings (e.g., the rigid rings may extend over proximal and distal ends of the balloon and compress them against the interior shaft, or the proximal and distal ends of the balloon may be mounted to the rigid rings which are themselves mounted to the interior shaft). In some embodiments, the balloon is fixed to the interior shaft without the need for additional elements (e.g., the elasticity of the proximal and distal ends of the balloon may allow these ends to hold tightly to the interior shaft to the extent necessary to prevent axial motion or leakage of fluids). In some embodiments, the balloon is not directly fixed to the interior shaft, but is held in place by, for example, electrodes positioned about the exterior of the balloon.

The balloon can be made of compliant material (e.g., silicone, latex) or noncompliant material (e.g., PVC, PE, PET). For example, it a procedure involves expanding a body lumen or other anatomical site to a particular size, a suitably-sized noncompliant balloon may be used. For example, if a procedure involves expansion to an uncertain or various size(s), a suitable compliant balloon may be used. The balloon material can be porous or non-porous with respect to the fluid used for inflation (e.g. saline). The balloon can be any configuration or shape (e.g. tubular, spherical) and can be various sizes, allowing the balloon to be designed for myriad therapies. The size and shape of the balloon when inflated a given inflation amount can be tailored based on the anatomical site(s) where the balloon is intended to be deployed for an electrosurgical operation, as well as the size of the patient (e.g., sized for adult anatomies (i.e., a comparatively large balloon size) or sized for infant anatomies (i.e., a comparatively small balloon size)).

The electrosurgical balloon can be provided with a monopolar electrode system or a bipolar electrode system. The electrode(s) can be configured to provide an appropriate wattage for the treatment. For example, for bipolar RF treatments in some embodiments, the bipolar electrodes of the electrosurgical balloon can be supplied with RF energy in a range of from about 2 to about 60, from about 10 to about 50, from about 15 to about 45, or from about 10 to about 30 watts. In some embodiments, an electrosurgical procedure is conducted with the bipolar electrodes of the electrosurgical balloon using about 18 watts of RF energy. The level of electrical power used in conjunction with a bipolar system (as well as monopolar system) can be varied and optimized for a particular application, and, if sufficiently high, can generate heat sufficient to dissect, coagulate, or otherwise heat-treat the tissue to which it is applied. This can be used for a variety of surgical procedures, such as, for example, blunt dissection. Exemplary tissue treatment procedures that can employ the devices described herein include, for example, dissection and coagulation as mentioned above, as well as blunt dissection with coagulation, spot coagulation, and coagulation of large tissue planes.

The inflation amount (measured by the internal pressure (e.g., psi) in the balloon) of a balloon can be adjustable, and can be adjusted to improve the conformability of the balloon to tissue surfaces, even on irregular tissue surfaces. Greater conformability of the balloon to the tissue surface can increase the electrode area in contact with tissue, which may result in reduced treatment times and/or reduced power requirements.

With a compliant balloon, adjusting the inflation amount can allow individualized size adjustments at the surgical site of a particular patient, and can also be used to adjust gaps between bipolar electrodes. For RF treatments, variation in the gap between bipolar electrodes can vary the RF application to the tissue. For example, the closer the bipolar electrodes are to each other the more focused the RF energy that is applied to the area between the electrodes, permitting deeper penetration of the RF energy into the tissue in that area.

With a non-compliant balloon, adjusting the inflation amount can allow control over the rigidity and extent to which the balloon holds its shape when subjected to external forces. A non-compliant balloon can assure a distance between electrodes and/or portions thereof, and ensure the inflated balloon size and shape is substantially maintained to a predetermined configuration, even at different inflation amounts (i.e., internal pressures).

In some embodiments, one or more of the electrode(s) are configured to deliver ultrasonic therapies. In some embodiments, the electrosurgical balloon is configured to provide both RF applications and ultrasonic applications.

In some embodiments, an electrode set is provided about the exterior surface of the balloon ("electrode set" is used herein to mean one or more electrodes). The electrode set may be bipolar, and may include one or more first electrodes (e.g., active electrodes) serving as a first pole of a bipolar electrode configuration and one or more second electrodes (e.g., return electrodes) serving as a second pole of the bipolar electrode configuration. The electrodes can be separated from each other about the balloon's exterior surface, and can be insulated from each other by the separation area formed by the non-conductive balloon substrate material.

In some embodiments, the electrodes have a tubular shape (i.e., the electrodes have a central axial lumen extending along their length). The cross-sectional shape of the electrodes can be any suitable shape, for example, circular, ovoid, triangular, square, or rectangular. In some embodiments, the wall of each electrode defining its tubular shape has a spiral configuration. In other words, the electrode may have a helical discontinuity extending along a portion of its length, or a portion of its length can be formed of coiled wire, such as, for example, a coiled extension spring (i.e., a close-coiled helical spring) having a helical discontinuity between adjacent turns of the coil. The coiled wire may have any suitable cross-sectional shape, such as, for example, circular, ovoid, triangular, square, or rectangular. Due to the spiral configuration, when the electrode is in a straight configuration, its wall may prevent passage therethrough of liquid and/or gas. Also due to the spiral configuration, when the electrode is in a bent configuration, portions of its wall may separate along the helical discontinuity, allowing passage therethrough of liquid and/or gas. In this way, an electrodes can maintain a working fluid (e.g., a conductive fluid such as, for example, saline) within its central axial lumen, which can be released when the electrode is bent. In some embodiments, each of the electrodes can be coupled to a single shared working fluid source. In some embodiments, a subset of electrodes are coupled to one working fluid source, while other electrodes and/or subsets of electrodes are coupled to one or more other working fluid sources. In some embodiments, each electrode is coupled to its own individual working fluid source. Working fluid sources can independently provide a fluid flow through the electrode or electrodes connected thereto, to dispense fluid from the bent portion of the electrode(s).

After delivery to the treatment site in its deflated state, the balloon, surrounded by a set of electrodes in a straight configuration, can be inflated with an inflation fluid. The inflation fluid can be a gas (e.g., air) or a liquid (e.g., saline). This inflation can cause the balloon to expand and push against the electrode set, causing portions of the electrode(s) to bend. In some embodiments, the inflation fluid can be cooled so as to cool the balloon. In some embodiments cooled inflation fluid can be circulated through the interior of the balloon while maintaining the same inflation of the balloon, in order to sustain a cooling effect. A working fluid (e.g., saline) can be delivered through the central axial lumens of each electrode, and dispensed from the bent portion of each electrode. In some embodiments, the working fluid can be delivered selectively to one, some, or all electrodes in a set, thereby controlling the areas of the treatment site to which working fluid is dispensed.

When the electrodes are energized, the dispensed working fluid can produce an electric coupling to the treatment site by providing conductive pathways for energy to flow among electrodes at the treatment site. In some embodiments, the electrodes in a set can be energized selectively so that one, some, or all electrodes in the set are energized. Further, the selectively energized electrodes can be energized in any combination of active and return electrodes (in a bipolar configuration), or the selectively energized electrode(s) can be energized in a monopolar configuration. Moreover, the dispensed fluid can mitigate any thermal expansion of the balloon arising from heat dissipating from the energized electrode(s).

The electrodes can be configured to release the working fluid under given conditions and/or at variable rates. The fact and rate of fluid release may be dependent on, for example, the extent to which the electrode has been bent (increased expansion of the balloon can cause greater bending of the electrode to allow fluid release and higher flow rate), the force with which the wall of an electrode presses against itself along its helical discontinuity (lesser force can contribute to fluid release and higher flow rate), the type of fluid used (fluid with smaller molecules or lower viscosity may contribute to fluid release and higher flow rate), and the pressure applied to the fluid (greater pressure may contribute to fluid release and higher flow rate).

In some embodiments, in addition to delivering working fluid, the electrodes (or selected electrodes) can be used to deliver drugs from a drug source to the treatment site. Drug delivery can be performed similarly to working fluid delivery as described herein, and may be performed in any combination with energization of electrodes or working fluid delivery through other electrodes. Thus, both electrosurgical and pharmaceutical-based therapies can be applied to the treatment site using the electrosurgical device.

In some embodiments, the electrosurgical device of any of the embodiments described herein can include a weeping balloon such as, for example, any of those disclosed in U.S. patent application Ser. No. 13/250,104, filed Sep. 30, 2011, which is incorporated herein in its entirety by reference thereto. The weeping balloons, electrodes, and other elements and techniques (e.g., manner of balloon attachment to the interior shaft, as discussed herein) disclosed in U.S. patent application Ser. No. 13/250,104 may be incorporated into the embodiments disclosed herein, as additions or alternatives to elements or techniques of the embodiments disclosed herein.

In some embodiments, the electrosurgical device can be slidably disposed within a lumen of an outer catheter. In some embodiments, the electrosurgical device can be fully retracted within the outer catheter so that the deflated balloon and electrodes can reside within the lumen of the outer catheter until deployed at the treatment site.

In some embodiments, the electrosurgical device in its deflated configuration can extend through the lumen of a 5 French (Fr) or larger catheter. In operation, the electrosurgical device (including the outer catheter if provided) can be delivered through a trocar to a percutaneous treatment site using a delivery system (e.g., a 5 Fr or larger trocar). As an example only and not by way of limitation, a delivery catheter can be inserted percutaneously (e.g., through an introduction port or trocar) and guided to a specific treatment site. A guidewire can be inserted through the delivery catheter to the treatment site. The delivery catheter can be removed, and the electrosurgical device can be advanced along the guidewire to the site. The balloon and electrodes can be extended from the outer catheter (if provided) at the site and inflated, causing the electrodes to bend and to release a working fluid (which can be selectively controlled as described herein). One or more electrodes of the electrode set around the balloon's exterior surface can be selectively energized and target tissue can be contacted with the energized balloon electrode tip. After the electrosurgical procedure is conducted, the guidewire and the electrosurgical device can be removed simultaneously or sequentially in any order. In some embodiments, a guidewire may not be used, and the electrosurgical device can be inserted through the delivery catheter to reach the target site. The delivery catheter may include a hemostasis valve to accommodate the electrosurgical device. In some embodiments, the electrosurgical device can be articulable (or can be used with an articulable catheter) such that it can navigate to a treatment site without use of a guidewire. In some embodiments, the electrosurgical device can be inserted and manipulated through a bronchoscope or endoscope, instead of using a delivery catheter and/or guidewire.

The electrosurgical device according to some embodiments presented herein allows increased surface area to be in contact with targeted tissue beyond the size limitations of an introduction port (e.g., a standard 5 mm trocar diameter for typical laparoscopic instruments). Thus, the electrosurgical device allows delivery of a large electrode system through a small introduction port, by allowing a working portion of the electrosurgical device to be introduced through the port in a straight (non-expanded) configuration, which can transition to an expanded configuration at a target tissue site. The electrosurgical device can allow electrosurgical procedures to be conducted using an electrode system that has a size and shape to achieve desired functionality and performance capabilities at the surgical site, with minimal or no size restrictions arising from the diameter of a trocar and/or delivery catheter.

Embodiments of the electrosurgical device described herein can be used for many procedures, including percutaneous treatment of aneurysms, control of bleeding, treatment of mitral valve regurgitation by tightening the annulus around the mitral valve, treatments in the upper and lower gastrointestinal tract (GI) (including, e.g., bleeding varices, ulcers, caustic poisons, Crohn's disease, Barrett's disease), diverticulosis, varicose veins, sympathetic nerves (e.g., renal denervation by RF ablation), tumors, gene and stem cell therapies, and other surgical procedures in which treatment can include vessel sealing/coagulation, tissue shrinkage, and/or tissue ablation.

To further illustrate electrosurgical devices disclosed herein, exemplary embodiments will now be described with reference to the Figures. It should be understood that any features of an embodiment disclosed herein can be combined with any features of any other embodiment disclosed herein, without departing from the scope of the present disclosure. Thus, any of the features of the electrosurgical devices described herein (e.g., those discussed above) can be combined with any features of other electrosurgical devices described herein (e.g., the exemplary embodiments described below with reference to the Figures).

Figure 2:
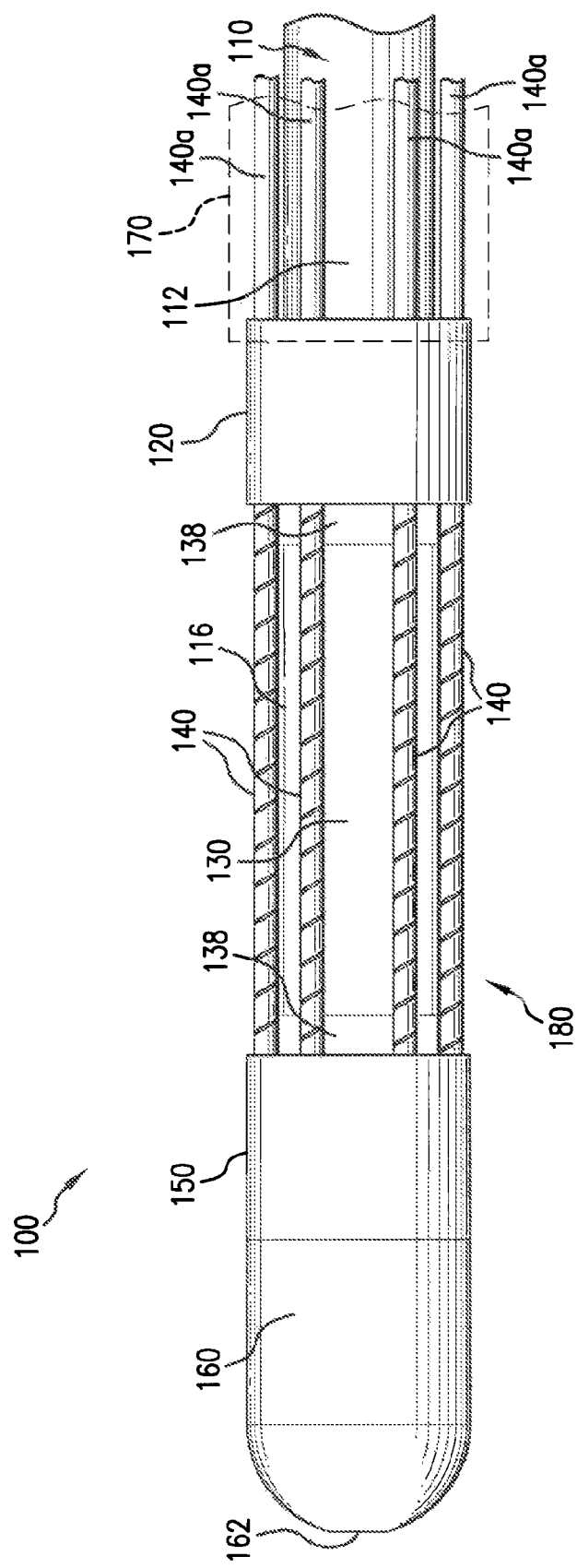
FIG. 2 illustrates a side view of the electrosurgical device of FIG. 1 in a straight configuration, according to an embodiment presented herein.
Figure 3:
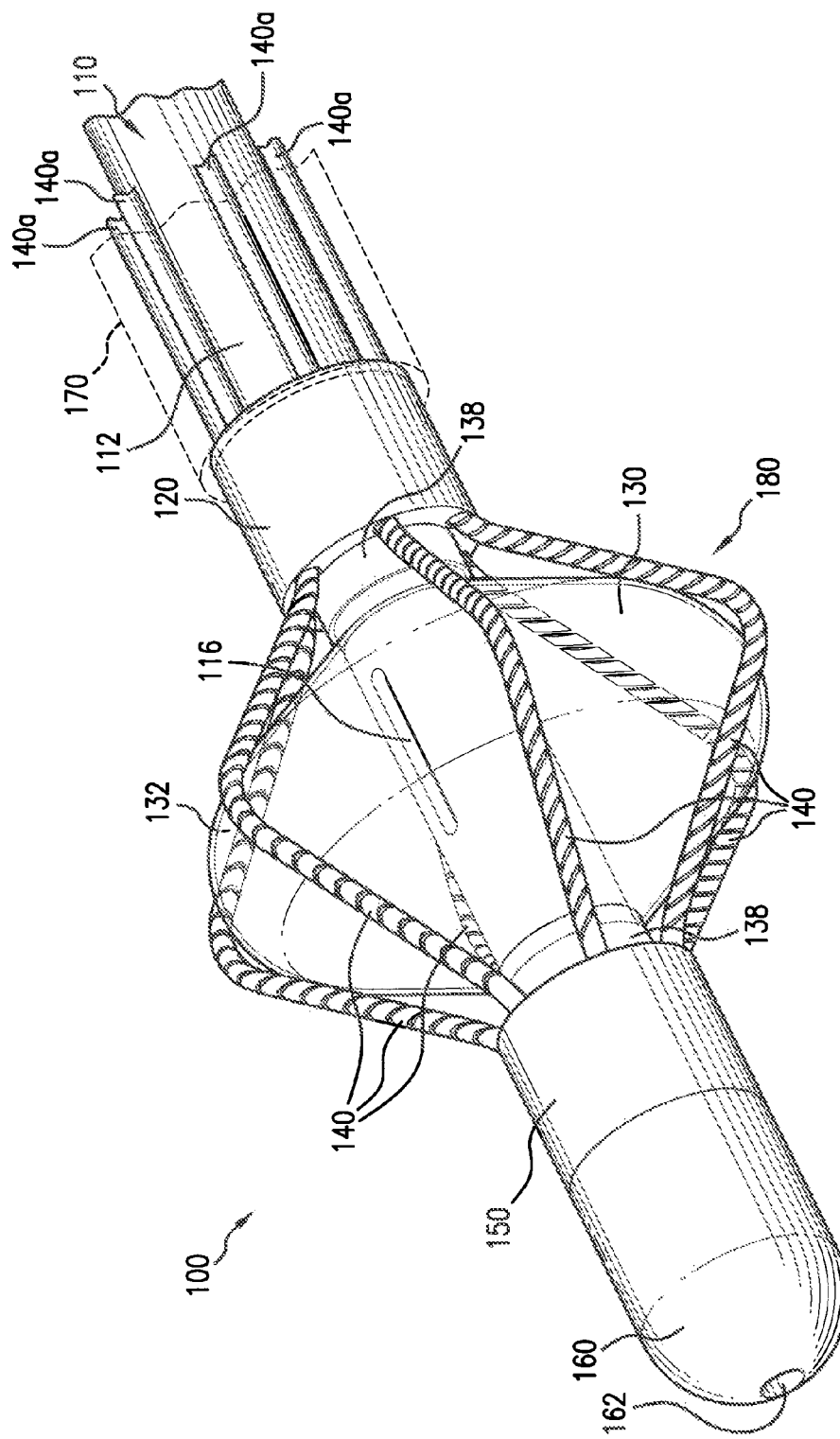
FIG. 3 illustrates a perspective view of the electrosurgical device of FIG. 1 in an expanded configuration, according to an embodiment presented herein.
Figure 4:
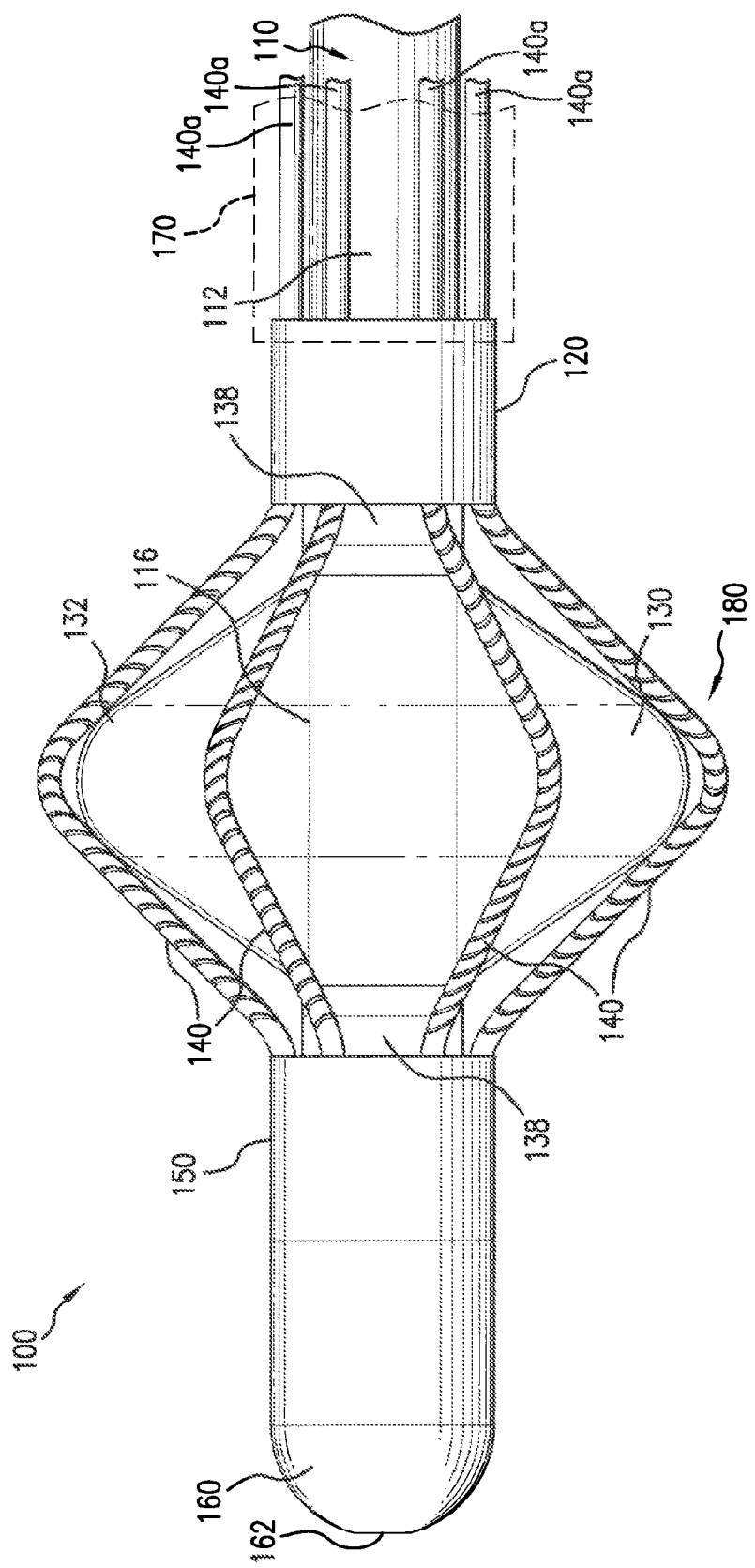
FIG. 4 illustrates a side view of the electrosurgical device of FIG. 1 in an expanded configuration, according to an embodiment presented herein.

FIGS. 1-4 illustrate an exemplary electrosurgical device 100 according to an embodiment presented herein. Electrosurgical device 100 includes a tubular interior shaft 110, bolt circles 120 and 150, a balloon 130, one or more electrode(s) 140, and an introducer tip 160. In some embodiments, electrosurgical device 100 includes an exterior shaft 170. In some embodiments, electrosurgical device 100 can be used as part of a catheter assembly, e.g., passed through a catheter (exterior shaft 170 can be such catheter or a sheath or shaft thereof), and/or constructed as a catheter (with exterior shaft 170 as a catheter sheath or shaft). For example, in some embodiments, exterior shaft 170 can define the working lumen of a bronchoscope, through which electrosurgical device 100 passes. Electrosurgical device 100 can have a working portion 180 along its length corresponding to the length of electrodes 140 between bolt circles 120 and 150. FIGS. 1 and 2 illustrate working portion 180 in a straight (non-expanded) configuration, and FIGS. 3 and 4 illustrate working portion 180 in an expanded configuration.

Figure 5:
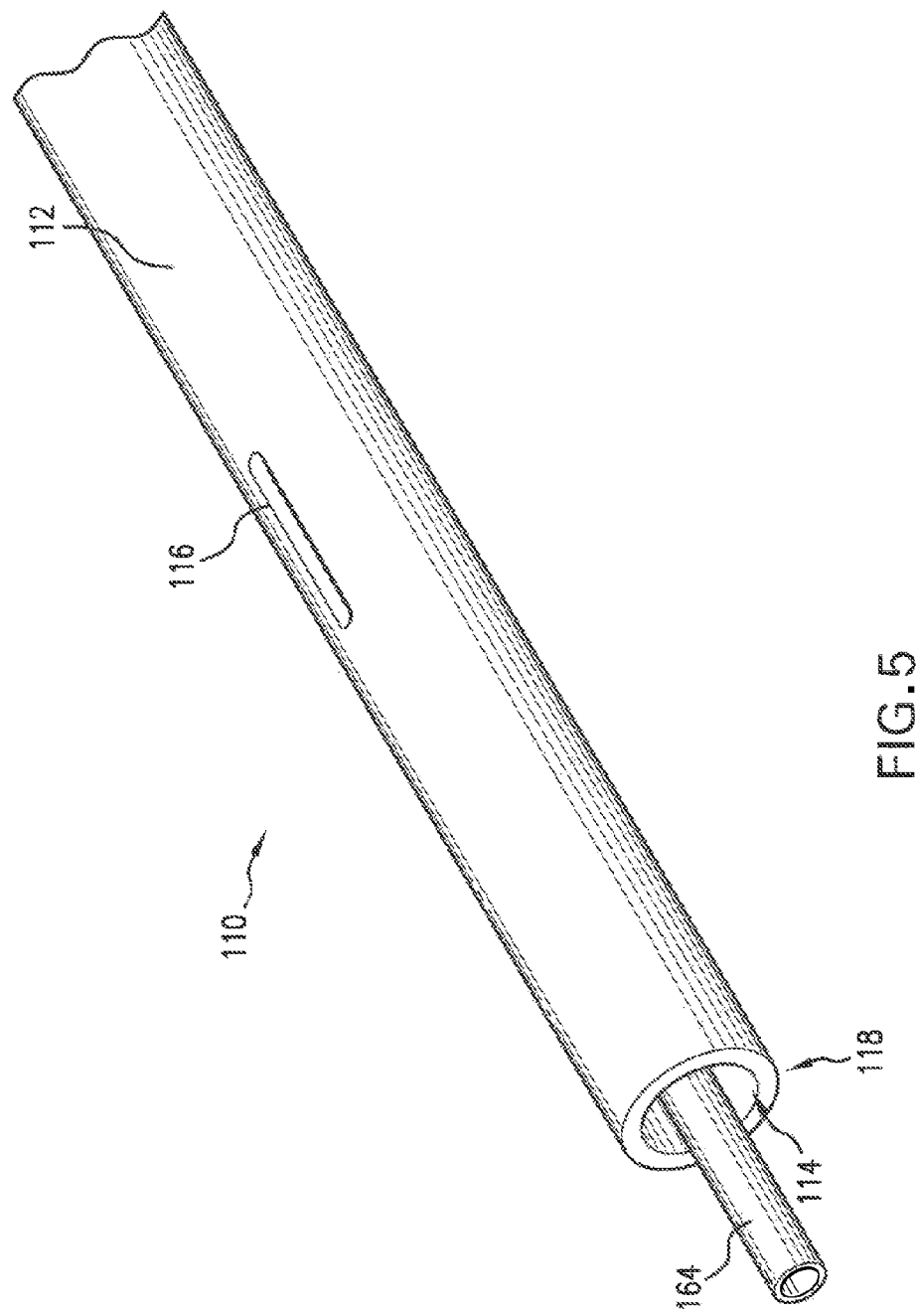
FIG. 5 illustrates a perspective view of an interior shaft of the electrosurgical device of FIG. 1, according to an embodiment presented herein.

Interior shaft 110 has an elongated body 112 with a central axial lumen 114 and an opening 116 (see FIG. 5). Lumen 114 can extend from a proximal end portion (not shown) to a distal end portion 118, or at least to an extent suitable to provide fluid communication between the proximal end portion and opening 116. In some embodiments a guidewire shaft 164 is disposed within lumen 114 (see FIG. 5), to allow a guidewire to pass through electrosurgical device 100 without contacting fluid within lumen 114. In some embodiments, lumen 114 can accommodate one or more fluid delivery lines (which may be coupled to opening(s) 116), and/or can accommodate a guidewire therethrough. Interior shaft 110 can extend through a central bore 122 of proximal bolt circle 120 such that a distal portion of interior shaft 110 extends distally beyond a distal end of proximal bolt circle 120. Opening 116 can be defined through the wall of interior shaft 110 in the distal portion of interior shaft 110. Interior shaft 110 can define a plurality of openings 116.

Balloon 130 can be disposed about the exterior of interior shaft 110, corresponding to at least a portion of working portion 180. Balloon 130 can define an interior chamber 132 in fluid communication with lumen 114 of interior shaft 110, via opening 116. Balloon 130 can include a proximal opening 134 and a distal opening 136, through which interior shaft 110 can extend (see FIGS. 8 and 9). Proximal and distal openings 134 and 136 can be sealably coupled to the exterior of interior shaft 110 (i.e., such that a working fluid cannot pass from interior chamber 132 to an exterior of balloon 130 via the coupling of proximal and distal openings 134 and 136 to interior shaft 110 under expected working conditions). Proximal and distal openings 134 and 136 can be disposed such that opening 116 is between proximal opening 134 and distal opening 136. In some embodiments, proximal and distal openings 134 and 136 are sealably coupled to the exterior of interior shaft 110 by elasticity of the openings 134 and 136 (e.g., by an interference fit between proximal and distal end portions of balloon 130 and the exterior of interior shaft 110). In some embodiments, proximal and distal openings 134 and 136 are sealably coupled to the exterior of interior shaft 110 by rings 138 (see FIGS. 1-4). In some embodiments, rings 138 can extend around an exterior of balloon 130 at proximal and distal portions thereof and can apply pressure to proximal and distal portions of balloon 130 to couple balloon 130 to interior shaft 110 (e.g., proximal and distal portions of balloon 130 can be pressed between rings 138 and interior shaft 110). In some embodiments, balloon 130 is coupled to interior shaft 110 and/or to rings 138 by, for example, press fit, interference fit, adhesive, and/or co-molding. In some embodiments, balloon 130 can be otherwise sealably attached to rings 138, which are in turn coupled to interior shaft 110 (e.g., by an interference fit between rings 138 and the exterior of interior shaft 110).

Balloon 130 can be inflated with an inflation fluid (e.g., gas or liquid). For example, in response to application of fluid pressure (e.g., inflation fluid applied through lumen 114, through opening 116, and into interior chamber 132) balloon 130 can inflate (i.e., expand to an expanded configuration). Balloon 130 may be configured to deflate (i.e., return to an uninflated configuration) in the absence of (or in response to negative) fluid pressure. In some embodiments, the inflation fluid can be cooled so as to cool balloon 130 (which can become heated when electrode(s) 140 are energized). In some embodiments cooled inflation fluid can be circulated through the interior of balloon 130 while maintaining the same inflation (i.e., fluid pressure) of balloon 130, in order to sustain a cooling effect.

Figure 8:
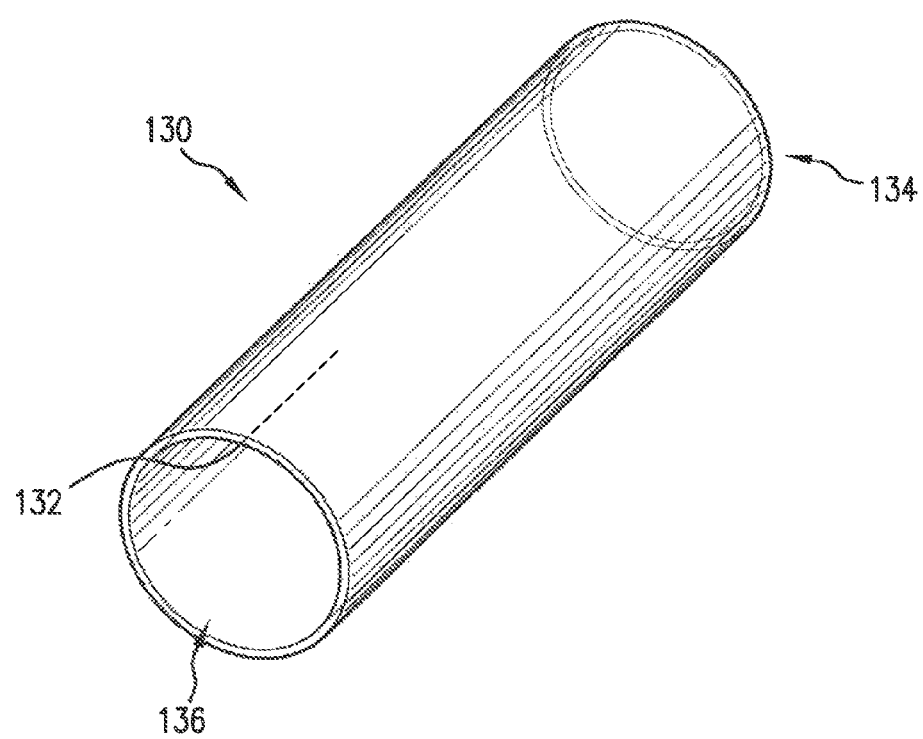
FIG. 8 illustrates a perspective view of a balloon of the electrosurgical device of FIG. 1 in an uninflated configuration, according to an embodiment presented herein.
Figure 9:
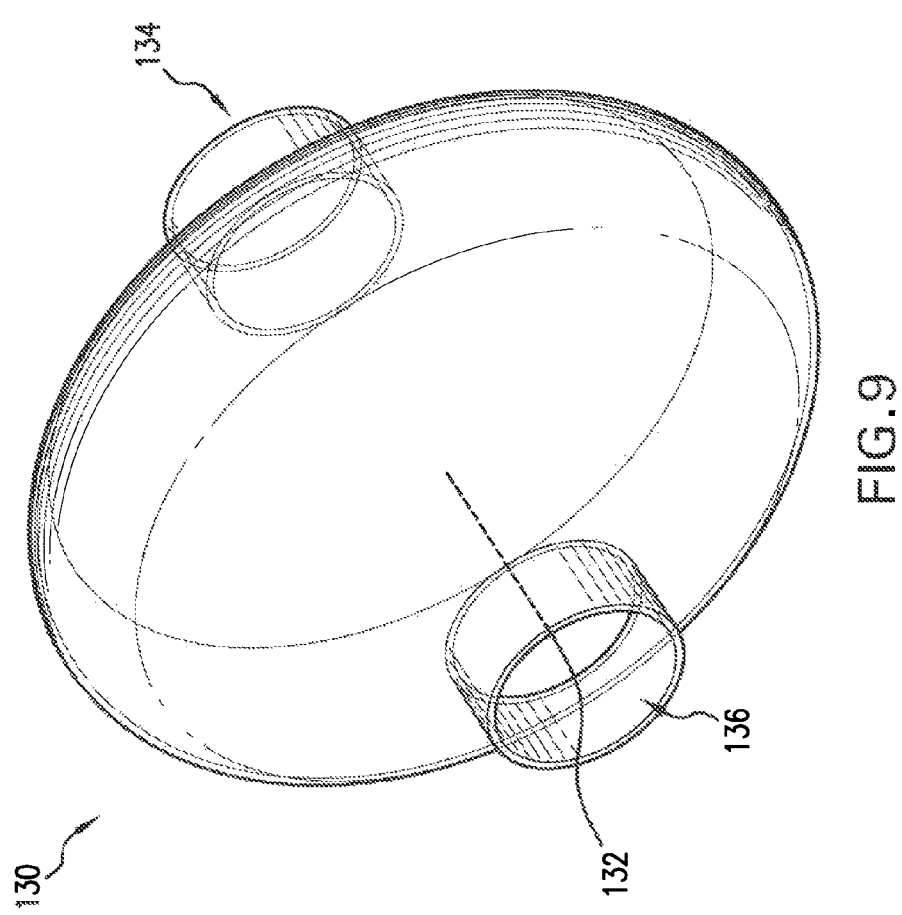
FIG. 9 illustrates a perspective view of the balloon of FIG. 8 in an expanded configuration, according to an embodiment presented herein.

In an uninflated configuration, balloon 130 may conform to the exterior contour of interior shaft 110 (e.g., may be cylindrical, defining a cylindrical interior chamber 132, see FIG. 8). In an expanded configuration, balloon 130 may take any suitable shape (see, e.g., the exemplary balloons 130 shown in FIGS. 9 and 17). Balloon 130 can be compliant or noncompliant (i.e., by being made of a compliant or noncompliant material, respectively).

Figure 6:
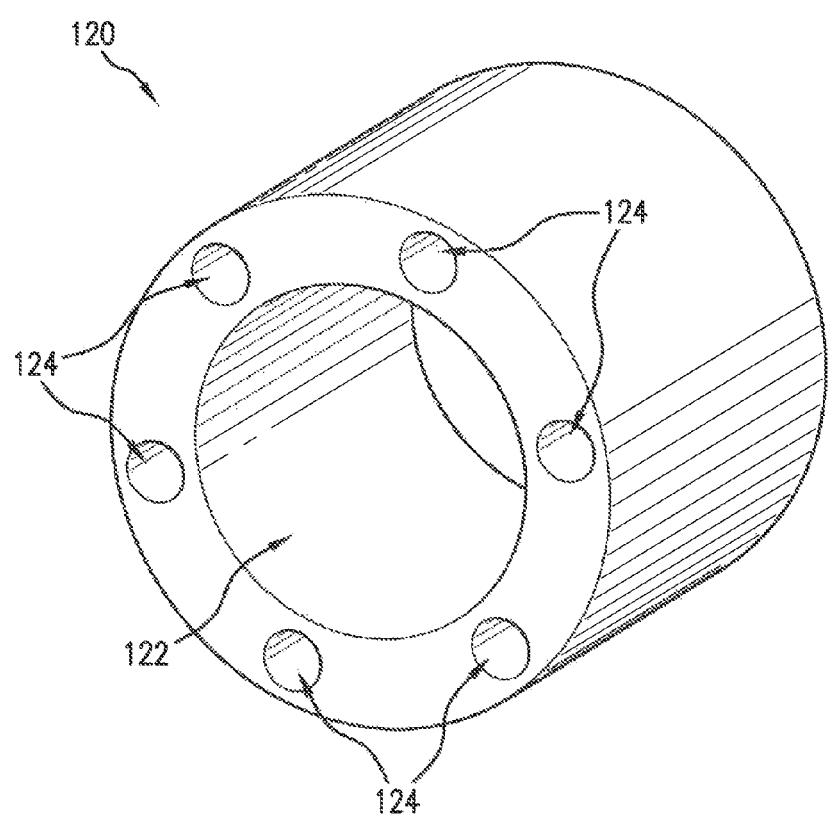
FIG. 6 illustrates a perspective view of a bolt circle of the electrosurgical device of FIG. 1, according to an embodiment presented herein.
Figure 7:
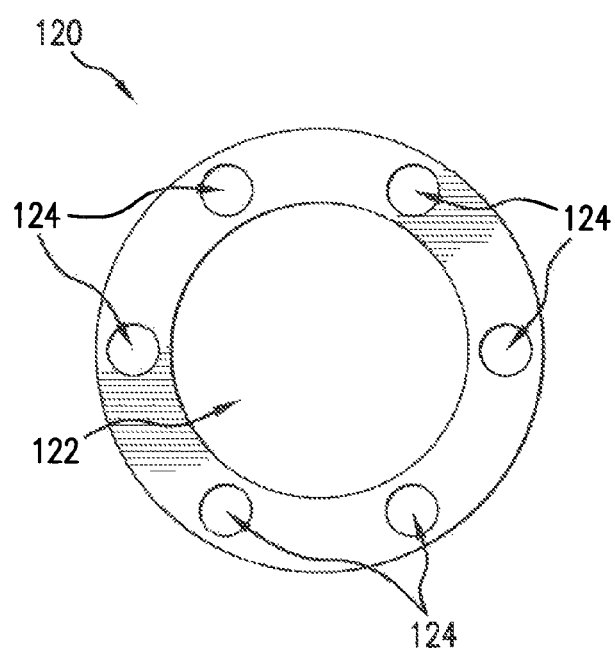
FIG. 7 illustrates a plan view of the bolt circle of FIG. 6, according to an embodiment presented herein.

Proximal bolt circle 120 can be coupled to interior shaft 110 proximally adjacent to balloon 130. As shown in FIGS. 6 and 7, proximal bolt circle 120 can define a central longitudinal bore 122 configured to correspond to the exterior of interior shaft 110, as described herein. Proximal bolt circle 120 can define one or more radial bores 124 disposed radially around central longitudinal bore 122, each configured to correspond to the exterior contour (e.g., exterior diameter) of a proximal portion 140a of an electrode 140, as described herein. Proximal bolt circle 120 can be coupled to interior shaft 110 using any suitable technique as would be apparent to one of skill in the art. For example, proximal bolt circle 120 can be coupled to interior shaft 110 via press fit, adhesive, or mechanical fasteners. In some embodiments, proximal bolt circle 120 is integral with interior shaft 110, which together form a monolithic structure. In some embodiments, proximal bolt circle 120 can extend over a proximal portion of balloon 130 to sealably couple balloon 130 to the exterior of interior shaft 110 (e.g., replacing and performing the above-described function of proximal ring 138).

Distal bolt circle 150 can be coupled to interior shaft 110 distally adjacent to balloon 130. Distal bolt circle 150 can define a central longitudinal bore (similar to central longitudinal bore 122 of proximal bolt circle 120) configured to correspond to the exterior of interior shaft 110, as described herein. Distal bolt circle 150 can define one or more radial bores (similar to radial bores 124 of proximal bolt circle 120) disposed radially around central longitudinal bore 122, each configured to correspond to the exterior contour of a distal portion of an electrode 140, as described herein. In some embodiments, the central longitudinal bore is a partial bore. In such an embodiment, the partial central longitudinal bore can extend from a proximal face of distal bolt circle 150 toward a distal face thereof without reaching the distal face, so as to not extend completely through distal bolt circle 150. In some embodiments, each of the radial bores is a partial bore. In such an embodiment, the partial radial bore can extend from a proximal face of distal bolt circle 150 toward a distal face thereof without reaching the distal face, so as to not extend completely through distal bolt circle 150. Distal bolt circle 150 can be coupled to interior shaft 110 using any suitable technique as would be apparent to one of skill in the art. For example, distal bolt circle 150 can be coupled to interior shaft 110 via press fit, adhesive, or mechanical fasteners. In some embodiments, distal bolt circle 150 is integral with interior shaft 110, which together form a monolithic structure. In some embodiments, distal bolt circle 150 can extend over a distal portion of balloon 130 to sealably couple balloon 130 to the exterior of interior shaft 110 (e.g., replacing and performing the above-described function of distal ring 138).

Introducer tip 160 can be disposed distally adjacent to distal bolt circle 150. Introducer tip 160 may be sized and shaped to facilitate introduction and navigation of electrosurgical device 100 into and through areas of a body to position electrodes 140 at a target location at or adjacent to target tissue. Introducer tip 160 may define a central bore 162 (which may be aligned with and coupled to a guidewire lumen 164) to accommodate a guidewire therethrough. The size and shape of introducer tip 160 can be any that would be suitable for introduction and navigation for a particular procedure, or that would be suitable generally for a variety of procedures, for example, rounded (as shown), conical, cylindrical, or hook-shaped. Introducer tip 160 can be coupled to distal bolt circle 150, to interior shaft 110, or both, via any suitable technique as would be apparent to one of skill in the art. In some embodiments, introducer tip 160 is a monolithic structure that integrally includes one or both of distal bolt circle 150 and interior shaft 110.

In some embodiments, exterior shaft 170 includes a number of radial bores (which can correspond to the number of electrodes 140) to accommodate proximal portions 140a of electrodes 140 therethrough (see FIG. 3). Exterior shaft 170 can include a central bore to receive interior shaft 110 therethrough.

Electrodes 140 can be disposed so that a portion of each electrode 140 extends between proximal bolt circle 120 and distal bolt circle 150. In some embodiments, a distal end of each electrode 140 is fixed to distal bolt circle 150 (e.g., within a radial bore of distal bolt circle 150). In some embodiments, proximal portion 140a of each electrode 140 is slidably disposed through proximal bolt circle 120 (e.g., through a respective radial bore 124 of proximal bolt circle 120). In some embodiments, an electrode 140 extends between coaxial radial bores of proximal bolt circle 120 and distal bolt circle 150, (i.e., extending parallel to interior shaft 110 as shown in FIGS. 1 and 2). In some embodiments, an electrode 140 extends between non-coaxial radial bores of proximal bolt circle 120 and distal bolt circle (i.e., electrode 140 itself is in a helical configuration about interior shaft 110 as shown in FIG. 20). One or more electrodes 140 can be disposed about the exterior circumference of balloon 130, at regular intervals (e.g., equidistantly spaced apart, as shown) or at irregular intervals (e.g., different spacing between adjacent electrodes). In some embodiments, electrodes 140 are not directly coupled to balloon 130. In some embodiments, electrodes 140 are coupled to balloon 130 (e.g., via adhesive). For example, as shown in FIGS. 1-4, six electrodes 140 are disposed about the exterior of balloon 130. Electrodes 140 can be in a straight configuration corresponding to balloon 130 being in an uninflated configuration (as shown in FIGS. 1 and 2), or a bent configuration corresponding to balloon 130 being in an expanded configuration (as shown in FIGS. 3 and 4). In a straight configuration, electrodes 140 can retain working fluid within their respective electrode lumens 142, and in a bent configuration, electrodes 140 can release working fluid from within their respective electrode lumens 142 where bent.

Electrode(s) 140 are formed of a conductive, flexible, resilient material, such as, for example, stainless steel, nitinol, or a conductive polymer. In some embodiments, electrode 140 is alternatively formed of a nonconductive material, such as, for example, a nonconductive polymer, with a conductive coating applied to at least a portion of its outer surface, such as, for example, conductive paint or conductive ink. For example, electrode 140 can have a tubular shape, defining a central electrode lumen 142. The cross-sectional shape of an electrode 140 can be any suitable shape, for example, circular, ovoid, triangular, square, rectangular. Electrodes 140 can be of any suitable diameter as would be apparent to one of skill in the art, for example, from 1 French (Fr) to 6 Fr (i.e., from ⅓ millimeters (mm) to 2 mm).

Figure 10:
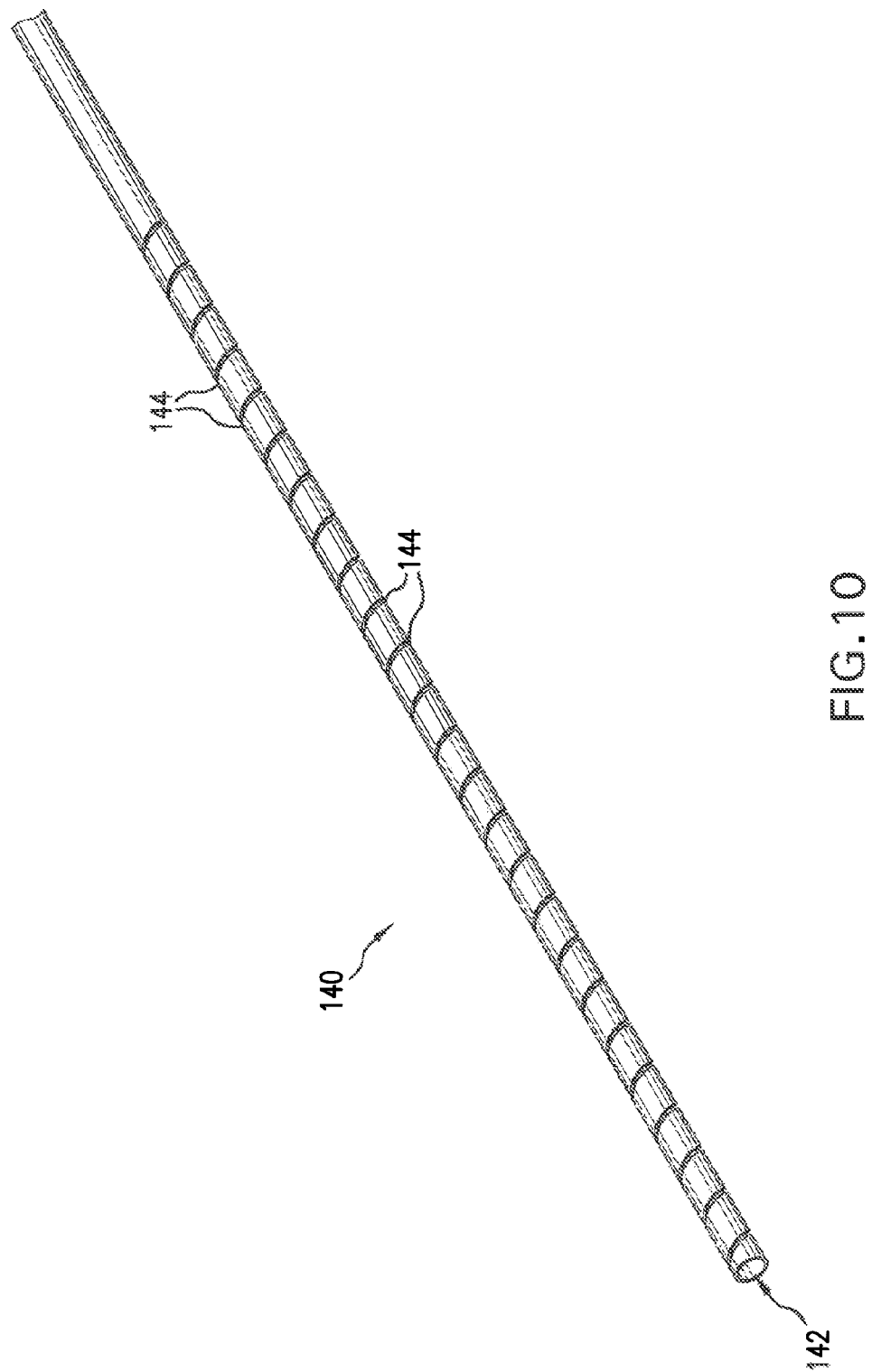
FIG. 10 illustrates a perspective view of an electrode of the electrosurgical device of FIG. 1 in a straight configuration, according to an embodiment presented herein.

In some embodiments, the wall defining the shape of electrode 140 has a spiral configuration, as shown in FIG. 10. For example, electrode 140 can be cylindrical with a helical discontinuity 144 extending along a portion of its length, or can be formed along a portion of its length of coiled wire. The coiled wire may have any suitable cross-sectional shape, such as, for example, circular, ovoid, triangular, square, or rectangular. In some embodiments, helical discontinuity 144 can be formed by a laser cut extending helically along electrode 140). In some embodiments, electrode 140 can be formed along a portion of its length of a coiled extension spring (i.e., a close-coiled helical spring) having a helical discontinuity 144 between adjacent turns of the coil. In some embodiments, electrode 140 may include one or more discontinuities that are not helical, for example, holes or slots cut through the wall of electrode 140. As would be appreciated by one of skill in the art, the characteristics of the discontinuities of electrode 140 can influence the shape and rigidity of electrode 140. For example, electrode 140 may define more closely-spaced discontinuities in an area where a smaller bending radius is desired, or electrode 140's helical discontinuity may include turns that are more closely-spaced at such an area. As the concentration of discontinuity in an area of electrode 140 increases, so does the flexibility and tendency to bend in that area. As would be recognized by one of skill in the art, the bending characteristics (e.g., shape, ease of bending) of electrode 140 can be controlled by the character of discontinuity of electrode 140. For example, and a desired character of discontinuity can be achieved by laser-cutting the discontinuity into a tubular electrode that forms electrode 140.

In some embodiments, a proximal end of each electrode 140 can extend proximally beyond a proximal face of proximal bolt circle 120, for example, to a proximal end of electrosurgical device 100 (or a catheter sheath (e.g., exterior shaft 170) containing electrosurgical device 100). In some embodiments, proximal ends of electrodes 140 can be individually electrically coupled to one or more power sources, for example, a radio-frequency (RF) generator or an ultrasonic generator. The power source(s) can be configured to selectively energize each electrode 140 independently of other electrodes 140. In some embodiments, one or more electrodes 140 are connected to one type of power source (e.g., an RF generator), and one or more electrodes 140 are connected to another type of power source (e.g., an ultrasonic generator).

Each electrode 140 can be coupled to a fluid source, which can be incorporated into electrosurgical device 100 (e.g., at a proximal end of electrosurgical device 100), or which can be separate from electrosurgical device 100, and coupled to electrode 140 proximal to proximal bolt circle 120 (e.g., a gravity- or pump-feed saline bag). Each electrode 140 of electrosurgical device 100 can be coupled to the same fluid source, each can be coupled to separate individual fluid sources, or subsets of electrodes 140 can be coupled together to a fluid source, while other electrodes 140 or subset(s) of electrodes 140 are coupled to other fluid source(s). In this way, the pressure and/or flow rate applied to fluid within electrode lumens 142 can be the same, or can be controlled individually or in groups.

In some embodiments, proximal ends of electrodes 140 can be individually fluidly coupled to one or more fluid sources. The fluid source(s) can be configured to selectively deliver fluid through electrode lumen 142 of each electrode 140 independently of electrode lumens 142 of other electrodes 140. Enabling energization and fluid delivery through selected electrodes 140 can provide configurability in the area of electrode device delivering treatment. For example, given a set of equally-spaced electrodes 140, energizing two adjacent electrodes 140 will provide a smaller treatment area than will energizing three adjacent electrodes 140, or two electrodes 140 with a non-energized electrode 140 in between). Further, enabling energization and fluid delivery through selected electrodes 140 can provide configurability in the depth of treatment. For example, energizing bipolar electrodes 140 spaced farther apart from each other will provide a shallower depth of treatment than will electrodes 140 spaced closer together.

The capability to energize selected individual electrodes 140 and to deliver fluid to selected individual electrodes 140 provides a user of electrosurgical device 100 with a variety of permutations of energizing and fluid delivery through electrodes 140. For example, an electrosurgical device 100 may include six electrodes 140, evenly distributed about balloon 130, each of which the user can select to apply with energy and/or working fluid.

In some instances, in the embodiment of electrosurgical device 100 having six electrodes 140, for example, the user may inflate balloon 130 to transform electrodes 140 into a bent configuration, and may energize all six electrodes 140 in a bipolar configuration, three as active electrodes, and three as return electrodes, each active electrode positioned immediately between two return electrodes, and vice versa. The user may simultaneously deliver conductive working fluid through all six electrodes 140. As the working fluid exits the electrodes, it can become energized and can create an electrical bridge between electrodes, delivering electrosurgical energy through the electrodes 140 and working fluid to target tissue for treatment. Having all six electrodes 140 energized and delivering fluid can provide a 360 degree working area (i.e., the area radially surrounding balloon 130 can be used to treat tissue). Alternatively, all six electrodes 140 can be energized in a monopolar arrangement.

In some instances, for example, the user may energize only two of the electrodes 140, one as an active electrode, and one as a return electrode, and may simultaneously deliver fluid from the two energized electrodes 140. The active electrode can be positioned adjacent the return electrode, and the working fluid can create an electrical bridge therebetween, to provide a 60 degree working area. Alternatively, the active electrode can be positioned with a non-energized intermediate electrode between it and the return electrode, and the working fluid can be delivered from each of the active and return electrodes, or from each of the active and return electrodes and the non-energized intermediate electrode. The working fluid can create an electrical bridge between the active and return electrodes, to provide a 120 degree working area. Alternatively, in any case, both energized electrodes 140 can be energized in a monopolar arrangement.

In some instances, for example, the user may energize only three of the electrodes 140, one as an active electrode, and two as return electrodes (or vice versa), and may simultaneously deliver fluid from the three energized electrodes 140. The active electrode can be positioned immediately between the two return electrodes (or the return electrode can be positioned immediately between the two active electrodes), and the working fluid can create an electrical bridge among these three energized electrodes 140, to provide a 120 degree working area. Alternatively, in any case, the three energized electrodes 140 can be energized in a monopolar arrangement.

In some instances, for example, the user may energize only three of the electrodes 140, one as an active electrode, and two as return electrodes (or vice versa), and may simultaneously deliver fluid from the three non-energized electrodes 140. The energized electrodes can be selected such that each is between two non-energized electrodes. The working fluid delivered from the non-energized electrodes can create an electrical bridge among the three energized electrodes 140, to provide a 360 degree working area. Alternatively, in any case, the three energized electrodes 140 can be energized in a monopolar arrangement.

As would be apparent to one of skill in the art, electrosurgical device 100 can be configured in a great many permutations in addition to the exemplary instances described herein, and can allow a user to tailor the configuration of device 100 to the requirements or goals of a particular procedure. To wit, each electrode 140 can be selectively configured to one of at least six states, as described herein: (1) fluid delivery on, energized as active electrode; (2) fluid delivery on, energized as return electrode; (3) fluid delivery on, not energized; (4) fluid delivery off, energized as active electrode; (5) fluid delivery off, energized as return electrode; (6) fluid delivery off, not energized. Consequently, given six electrodes each having six possible states, 46,656 permutations are possible ($6^6$). In some embodiments, the electrosurgical device includes more or fewer than six electrodes 140. For example, electrosurgical device 100 may include as few as one electrode or as many as the number of electrodes 140 that will fit side-by-side around the circumference of balloon 130, or around a desired portion thereof. The number of possible permutations increases with the number of electrodes, as does the resolution with which energy and fluid delivery can be controlled. For example, given six possible states for each electrode, 8 electrodes will provide 1,679,616 possible permutations ($6^8$), 12 electrodes will provide 2,176,782,336 possible permutations ($6^{12}$), and 20 electrodes will provide 3.65× $10^{15}$ possible permutations ($6^{20}$). It is noted that the above permutation calculations are for linear repeating permutations, and thus do not account for permutations that could be identical but for the orientation of electrosurgical device 100. These values are provided to represent the magnitude and configurability of electrosurgical device 100, and it should be understood that the actual number of possible permutations may be lower than provided, assuming embodiments where electrodes 140 are arranged at regular intervals, as would be understood by one of skill in the art.

In some instances, a user may selectively vary fluid flow rate through electrodes 140, may selectively vary the characteristics of energy applied to the electrodes 140, and/or may selectively vary the inflation amount of balloon 130 (thereby varying the shape of the bend of electrodes 140), dramatically increasing the potential configurations of electrosurgical device 100, by increasing the number of states available to each electrode. The flow rate of the working fluid can affect the thermal characteristics of the tissue. For RF applications, for example, the fluid can act as a heat sink, absorbing and carrying away excess or undesirable thermal energy resulting from electrically energizing electrodes 140. In cases where the working fluid is an electrically conductive fluid, the working fluid can also provide electrical dispersion by distributing the applied current over a larger surface area, thereby limiting the potential for undesirable thermal concentration. An uncontrolled or abundant flow rate can provide too much electrical dispersion and cooling at the electrode/tissue interface. On the other hand, a flow rate that is too low could lead to excessive heat and arcing.

Moreover, the working fluid can be used to help maintain temperatures within ranges conducive to coagulation of tissue (e.g., temperatures hot enough to denature the collagen and most soft tissue and bone, however not so hot that tissue is damaged to such an extent that it cannot be easily absorbed back into the body during a healing process) as opposed to charred, desiccated tissue. Collagen shrinkage, which causes coagulation, is a function of time and temperature. At 100° C., coagulation occurs substantially instantaneously, and at higher temperatures there will also be coagulation. Coagulation can begin at temperatures lower than 100° C., but the coagulation may occur more gradually. Without fluid (e.g., saline) present at the tissue being treated, temperatures can quickly rise above 100° C., and at such higher temperatures there is a greater likelihood of tissue sticking and charring. As one of skill in the art would appreciate, the time and temperature applied can be varied to suit a particular use. An RF power system can be controlled by suitable software to obtain desired power delivery characteristics. For example, in some embodiments, a control device or custom generator can be configured to allow the user to select a "pulse" mode of the RF power whereby the RF power to the balloon electrode tip is repeatedly turned on and off (e.g., at a rate of 100 cycles per second). Pulsed RF power may be characterized by a square wave, and may apply less heat than non-pulsed RF power. Pulsed RF power may help effectively treat thick tissues as would be would be recognized by one of skill in the art. Moreover, in some embodiments, fluid flow rates from electrodes 140 can be controlled based on the applied RF power to maintain temperatures at the treatment site within a desired range.

In embodiments described herein, saline has been provided as an exemplary electrically conductive working fluid for expelling through electrodes 140; however, other electrically conductive fluids may be used alternatively or additionally, consistent with the embodiments presented herein. Such electrically conductive fluids may also be used for filling balloon 130. The fluid for expelling through electrodes 140 and/or for filling balloon 130 may also comprise an electrically non-conductive fluid (e.g., deionized water and lactated ringers). The use of a non-conductive fluid for expelling through electrodes 140 still provides certain advantages over the use of a dry electrode including, for example reduced occurrence of tissue sticking to the electrodes of the devices disclosed herein, and cooling of the electrodes and/or tissue.

The inflation amount and internal pressure of balloon 130 can be varied to suit a particular use, and/or to assist in achieving desired electrode contact on tissue surface(s). Moreover, the inflation amount and internal pressure of balloon 130 can be varied to control the distance between portions of electrodes 140 if balloon 130 is made of a compliant material (e.g., a greater inflation amount and/or internal pressure can result in greater expansion of balloon 130, which can result in portions of electrodes 140 (e.g., portions of electrodes 140 located about a midplane of balloon 130 between proximal and distal ends of balloon 130) being positioned farther from each other). The inflation amount and internal pressure can be controlled by adjusting the amount of fluid dispensed into interior chamber 132 of balloon 130 (via opening 116).

Figure 12:
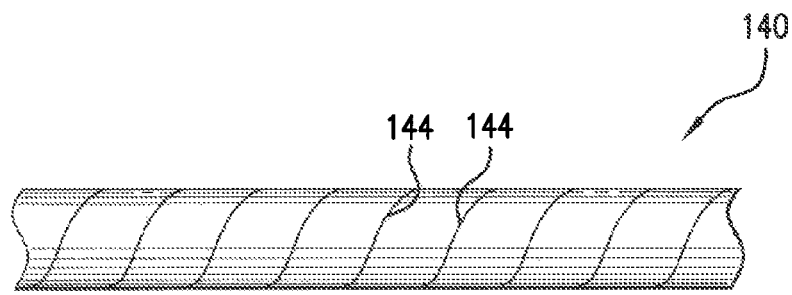
FIG. 12 illustrates an enlarged representative view of a portion of the electrode of FIG. 10 in a straight configuration, according to an embodiment presented herein.

In a straight configuration, as shown, for example, in FIGS. 10 and 12, the spiral configuration of an electrode 140 may define a closed electrode lumen 142, which does not allow working fluid within electrode lumen 142 to pass through walls of electrode 140 to an exterior thereof (e.g., through helical discontinuity 144). Working fluid may be prevented from passing through helical discontinuity 144 by, for example, the minimal width of the discontinuity (which, using current laser cutting technology, can be less than six thousandths of an inch). The width of the discontinuity can be small enough that the surface tension of the working fluid (e.g., saline) retained within electrode lumen 142 prevents it from passing through the discontinuity when not applied with external pressure, or when only applied with minimal external pressure (e.g., sufficient pressure to maintain working fluid within electrode lumen 142, but not to force working fluid through helical discontinuity 144).

Figure 11:
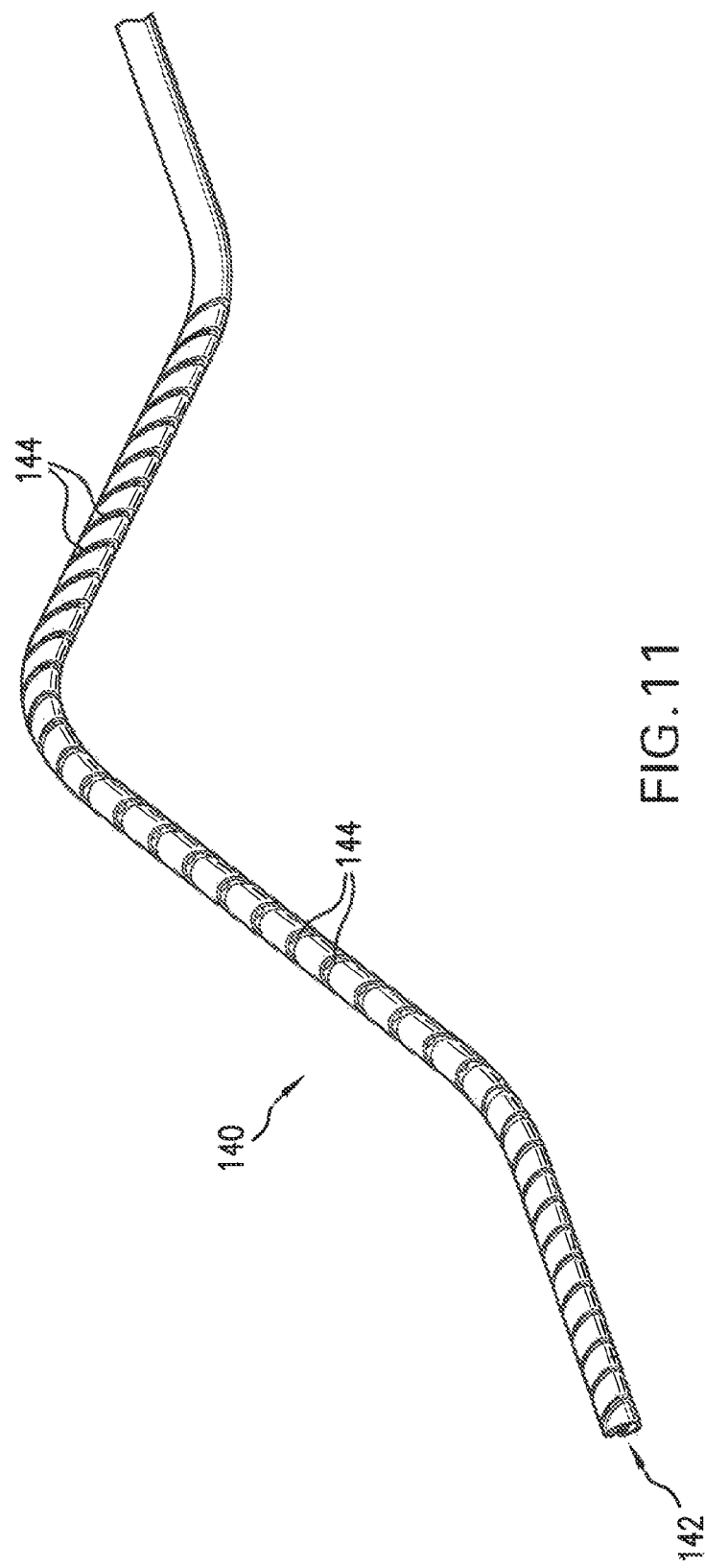
FIG. 11 illustrates a perspective view of the electrode of FIG. 10 in a bent configuration, according to an embodiment presented herein.
Figure 13:
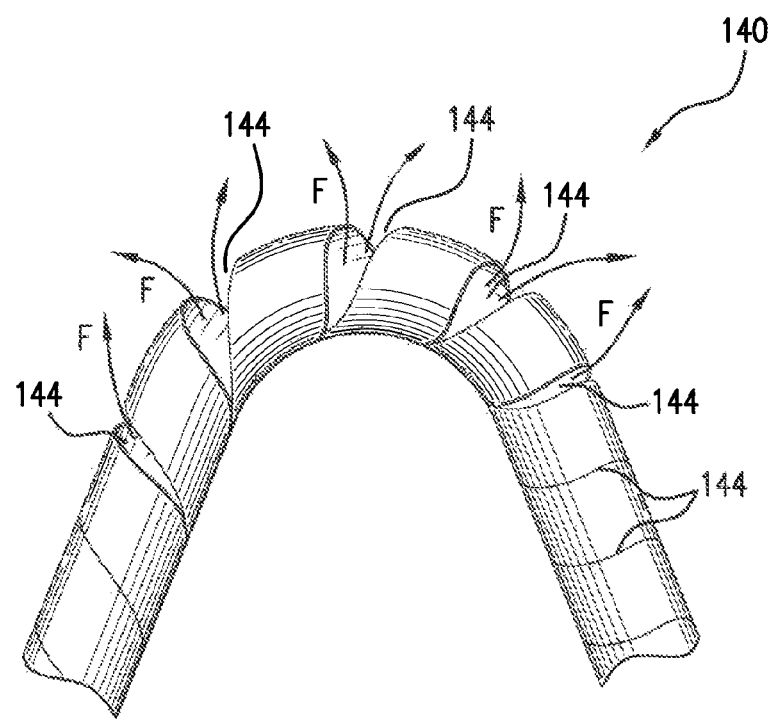
FIG. 13 illustrates an enlarged representative view of a portion of the electrode of FIG. 10 in a bent configuration, according to an embodiment presented herein.

In a bent configuration, as shown, for example, in FIGS. 11 and 13, the spiral configuration of an electrode 140 may define an open electrode lumen 142, which allows working fluid within electrode lumen 142 to pass through walls of electrode 140 to an exterior thereof (e.g., through helical discontinuity 144). FIG. 12 shows an enlarged representative view of the straight configuration of electrode 140 shown in FIG. 10. As seen in FIG. 12, helical discontinuity 144 does not define a space sufficient to release fluid at any point along the length of electrode 140. Thus, working fluid retained within electrode lumen 142 of electrode 140 cannot pass from within electrode lumen 142 through helical discontinuity 144 to an exterior of electrode 140. FIG. 13 shows an enlarged representative view of the bent configuration of electrode 140 shown in FIG. 11. As seen in FIG. 12, helical discontinuity 144 defines at least one space (five, as depicted) along the bent portion of the length of electrode 140. Thus, working fluid can pass from within electrode lumen 142 of electrode 140 through helical discontinuity 144 (at the openings) to an exterior of electrode 140. This fluid flow is represented in FIG. 13 by arrows F. As noted above, fluid flow rate through helical discontinuity 144 can be varied. In some embodiments, some or all of electrodes 140 of electrosurgical device 100 may release fluid at the same rate, at different rates, or not at all, even when in a bent configuration, depending on the application of fluid to electrode lumens 142.

One or more electrodes 140 may transition from the straight configuration (see FIGS. 1, 2, 10, 12) to the bent configuration (see FIGS. 3, 4, 11, 13) in response to inflation of balloon 130. As balloon 130 inflates, its exterior can push against electrodes 140 as shown in FIGS. 3 and 4, forcing them to bend (e.g., to conform to the exterior of the expanded balloon). Variation in the inflation amount of balloon 130 can influence at least the extent to which electrodes 140 bend, the shape of their bend(s), and the extent of their ability to release working fluid. For example, a greater inflation amount can result in a greater degree of bending in an electrode 140, which can result in a greater open area in helical discontinuity 144, allowing working fluid to be released at greater flow rates. Deflation of an inflated balloon 130 allows electrodes 140 to return to a straight configuration some embodiments, due to inherent resilience of electrodes 140) and a closed electrode lumen 142, whereby working fluid is retained therein.

In some embodiments, one or more electrodes 140 can be fixedly coupled (e.g., via adhesive, co-molding, press fit, or the like) to interior shaft 110 via distal bolt circle 150, and may be slidably coupled to interior shaft 110 via proximal bolt circle 120. When transitioning between straight and bent configurations, electrodes 140 may bend and straighten between proximal bolt circle 120 and distal bolt circle 150 (i.e., in working portion 180). In some embodiments, electrodes 140 can transition from the straight configuration to the bent configuration in response to forces applied thereto by expansion of balloon 130, and electrodes 140 can transition from the bent configuration to the straight configuration by the removal of such forces. In some embodiments, proximal bolt circle 120 is fixedly coupled to interior shaft 110, and electrodes 140 are slidably coupled to proximal bolt circle 120 (e.g., electrodes 140 can extend slidably through radial bores 124 of proximal bolt circle 120). In some embodiments, electrodes 140 are fixedly coupled to proximal bolt circle 120, and proximal bolt circle 120 is slidably coupled to interior shaft 110 (e.g., interior shaft 110 can extend slidably through central bore 122 of proximal bolt circle 120).

In some embodiments, electrodes 140 can be fixedly coupled to interior shaft 110 via both distal bolt circle 150 and proximal bolt circle 120. In such embodiments, electrodes 140 can stretch (e.g., due to their spiral configuration, inherent elasticity of material (if present), or both) between distal bolt circle 150 and proximal bolt circle 120 in response to expansion of balloon 130, and can release fluid due to opening(s) created in helical discontinuity 144 due to such stretching. In such embodiments, electrodes can return to their straight configuration in response to deflation of balloon 130.

In some embodiments, electrodes 140 are directly coupled to interior shaft 110, fixedly or slidably as described herein.

In some embodiments where electrode(s) 140 are formed of a conductive polymer, fluid opening(s) can be formed by one or more perforation(s) in the polymer (in lieu of or in addition to, helical discontinuity 144). The perforations can be configured such that the perforations open to release fluid only once the material surrounding the perforations expands so that the perforations open sufficiently large to permit fluid to flow therethrough. The perforations can be so opened by conductive polymer electrode 140 bending, fluid pressure within conductive polymer electrode 140 increasing, or both, so as to expand the material surrounding the perforations. The perforations can be configured to be closed when the conductive polymer electrode 140 is in the straight configuration.

Electrodes 140 can be formed with areas of varying rigidity along their lengths. For example, a working portion (corresponding to working portion 180) of an electrode 140 may be more flexible (e.g., in order to better conform to the shape of a balloon) while other portions may be more rigid (e.g., in order to maintain arrangement along the length of electrosurgical device 100). Electrodes 140 can form a variety of straight and expanded shapes (see, e.g., exemplary electrodes 140 shown in FIGS. 10, 11, and 14-16 (electrodes 140 are shown in FIGS. 14-16 without helical discontinuity 144 for clarity)), and may include preformed shapes (e.g., to accommodate balloon 130), as shown in, for example, FIGS. 14-16.

As an example to illustrate potential use of electrosurgical device 100, not to limit any aspect of electrosurgical device 100 or its use, a surgeon may desire to use electrosurgical device 100 in a bronchial tumor removal procedure. In such a case, the surgeon may fix an endotracheal tube in place within the patient, and may insert a bronchoscope through the patient's nasal passage. The surgeon may detect the tumor position and characteristics using the bronchoscope. The surgeon may insert a catheter with a coring tip through the bronchoscope to remove the tumor. The tissue site of the removed tumor may bleed due to the tumor removal (particularly if the tumor was highly vascularized). The surgeon may remove this catheter and insert electrosurgical device 100, which can be directed to the target tissue (in this case, the bleeding tissue at the site of the removed tumor). The surgeon may expand balloon 130 by inflating it with inflation fluid, causing electrodes 140 to transition from the straight configuration to the bent configuration. The surgeon may selectively deliver fluid through select electrodes 140, and may selectively energize select electrodes 140. The surgeon may change which electrodes 140 are energized and which electrodes 140 are delivering fluid as the procedure progresses. The surgeon may thereby deliver electrosurgical energy to seal the target tissue and prevent it from further bleeding. The surgeon may deflate balloon 130 and remove electrosurgical device 100.

It should be noted that, in a situation where a surgeon has begun treatment with a particular configuration of electrode energization and fluid delivery, the surgeon may change the configuration without removing and/or rotating electrosurgical device 100. This may be beneficial in a variety of cases, for example, where a surgeon misjudged the optimal configuration before beginning the procedure, or where the desired therapy characteristics change during a procedure (whether expected or not).

Figure 17:
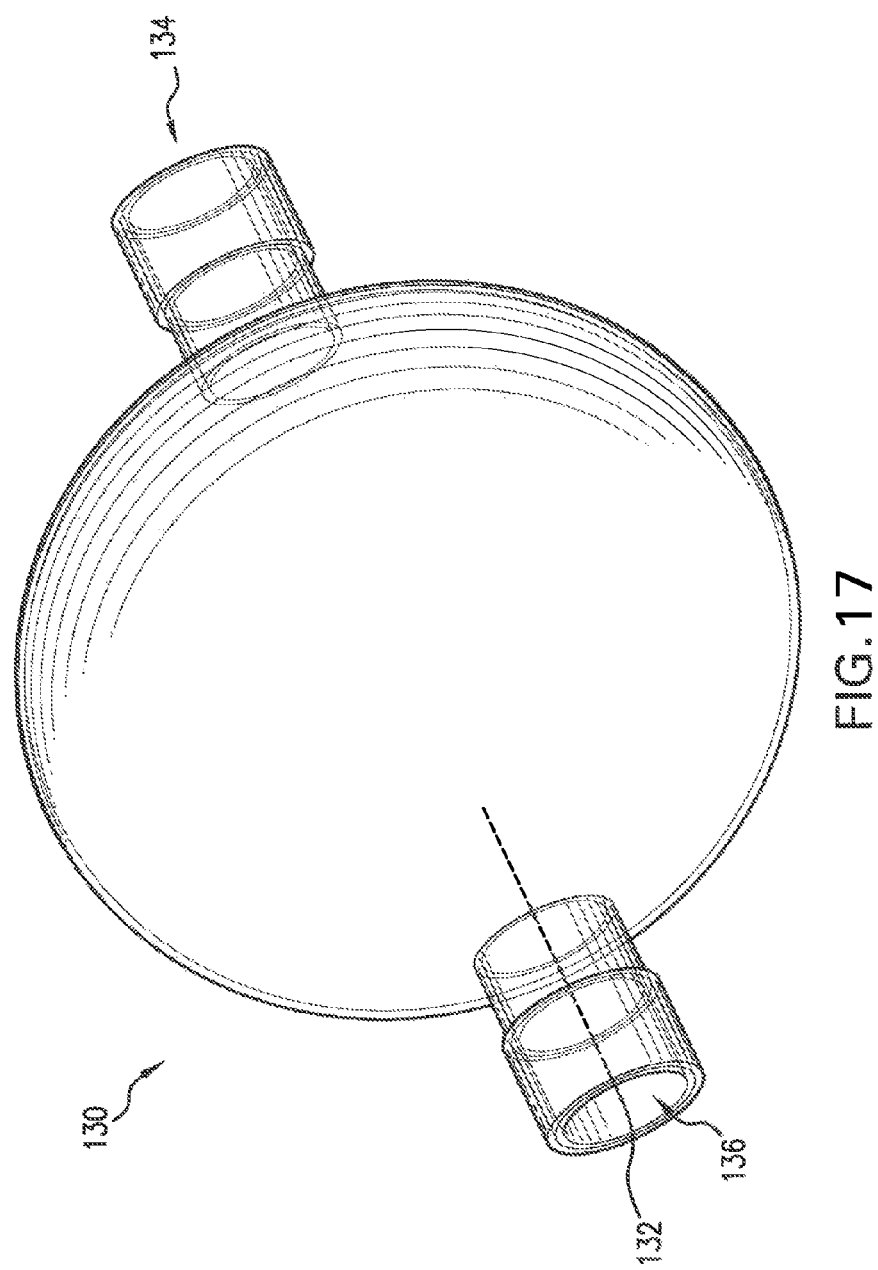
FIG. 17 illustrates a perspective view of a balloon of the electrosurgical device of FIG. 1 in an expanded configuration, according to an embodiment presented herein.

The foregoing description of the specific embodiments of the devices and methods described with reference to the figures will so fully reveal the general nature of the invention that others can, by applying knowledge within the skill of the art, readily modify and/or adapt for various applications such specific embodiments, without undue experimentation, without departing from the general concept of the present invention. For example, balloon 130 can have any configuration or shape (e.g., tubular, spherical, etc.) and can be various sizes, allowing the balloon to be designed for myriad therapies. FIG. 17 illustrates a perspective view of an exemplary balloon shape of balloon 130 according to embodiments presented herein.

Also, for example, in some embodiments electrosurgical device 100 does not include balloon 130. In such embodiments, where electrodes are slidably coupled to proximal bolt circle 120 and fixedly coupled to distal bolt circle 150, electrodes 140 can be transitioned between the straight configuration and the bent configuration individually by actuation at portions of electrodes 140 proximal to proximal bolt circle 120. For example, sliding a portion of a straight individual electrode 140 distally through a radial bore 124 of proximal bolt circle 120 can cause the portion of electrode 140 between proximal bolt circle 120 and distal bolt circle 150 to bend (i.e., transition to a bent configuration). For example, sliding a portion of a bent individual electrode 140 proximally through a radial bore 124 of proximal bolt circle 120 can cause the portion of electrode 140 between proximal bolt circle 120 and distal bolt circle 150 to straighten (i.e., transition to a straight configuration). In this way, electrodes 140 can independently transition between the straight configuration and the bent configuration without balloon 130. In some embodiments, electrosurgical device 100 includes an actuation mechanism at a proximal portion of thereof, which a user of electrosurgical device 100 can manipulate to selectively actuate sliding of one or more electrodes 140 through proximal bolt circle 120, and consequent bending of electrodes 140. For example, axial motion of electrodes 140 can be driven by any suitable technique as would be apparent to one of skill in the art (e.g., a push/pull rod or wire can be coupled to an electrode 140 and be accessible for actuation by a user of electrosurgical device 100). Such configuration of actuating bending of electrodes 140 independent of balloon 130 inflation can also be employed in an electrosurgical device 100 including balloon 130, in some embodiments.

Also, for example, in some embodiments where electrosurgical device 100 does not include balloon 130, where electrodes are fixedly coupled to proximal bolt circle 120 and proximal bolt circle 120 is slidably coupled to interior shaft 110, electrodes 140 can be transitioned between the straight configuration and the bent configuration together via axial motion of proximal bolt circle 120. For example, when in the straight configuration, axial motion of proximal bolt circle 120 distally toward distal bolt circle 150 can cause the portion(s) of electrode(s) 140 between proximal bolt circle 120 and distal bolt circle 150 to bend (i.e., transition to a bent configuration). When in the bent configuration, axial motion or proximal bolt circle 120 proximally away from distal bolt circle 150 can cause the portion(s) of electrode(s) 140 between proximal bolt circle 120 and distal bolt circle 150 to straighten (i.e., transition to a straight configuration). In this way, electrodes 140 can together transition between the straight configuration and the bent configuration without balloon 130. In some embodiments, electrosurgical device 100 includes an actuation mechanism at a proximal portion of thereof, which a user of electrosurgical device 100 can manipulate to actuate sliding of proximal bolt circle 120, and consequent bending of electrodes 140. For example, axial motion of proximal bolt circle 120 can be driven by any suitable technique as would be apparent to one of skill in the art (e.g., a push/pull rod or wire can be coupled to proximal bolt circle 120 and be accessible for actuation by a user of electrosurgical device 100). Such configuration of actuating bending of electrodes 140 independent of balloon 130 inflation can also be employed in an electrosurgical device 100 including balloon 130, in some embodiments.

Also, for example, in some embodiments where electrodes are fixedly coupled to proximal bolt circle 120 and proximal bolt circle 120 is slidably coupled to interior shaft 110, proximal bolt circle 120 can be rotated relative to interior shaft 110. Proximal bolt circle 120 can be rotated whether electrodes 140 are in the straight configuration or the bent configuration. Such rotation of proximal bolt circle 120 can cause the arrangement of electrode(s) 140 about interior shaft 110 to be helical. In some embodiments, proximal bolt circle can be limited to only axial motion and prevented from rotating with respect to interior shaft 110 (e.g., by being keyed to interior shaft 110).

Also, for example, in some embodiments electrodes 140 are pre-formed in the bent configuration (e.g., by being formed of a pre-formed resilient or shape memory material in the bent configuration), and are held in the straight configuration until released by a user and allowed to assume the bent shape (electrodes 140 may be held in (and released from) the straight configuration by any suitable mechanism that would be apparent to one of skill in the art, including, for example, a push/pull rod coupled to slidable proximal bolt circle 120, as described herein). Such embodiments may be particularly suitable where electrosurgical device 100 does not include balloon 130.

Also, for example, in some embodiments one or more electrodes 140 are formed of a material having a temperature-dependent shape, such as, for example, heat-setting nitinol. Such electrodes 14Q can be configured to change shape as they are heated (e.g., by electrosurgical energy). In some embodiments, temperature-dependent electrodes can be used to control temperature at a treatment site. Such electrodes 140 can, for example, be configured to increasingly bend with increasing heat at the treatment site. In embodiments where working fluid is released via such heat-dependent electrode 140, increased bending can allow working fluid (which may be cooled) to be released from electrode 140 at an increased rate, thereby maintaining/cooling the treatment site and electrode 140 at desired temperatures (e.g., at temperatures conducive to tissue coagulation). Thus, as one of skill in the art would appreciate, in such a case increased heat can trigger increased fluid flow and cooling, and vice versa, thereby controlling temperature at the treatment site.

Also, for example, in some embodiments electrosurgical device 100 may include or not include exterior shaft 170 as a part of electrosurgical device 100. In embodiments where exterior shaft 170 is not included as a part of electrosurgical device 100, electrosurgical device 100 can be used in conjunction with an exterior shaft 170 that is separate from electrosurgical device 100 (e.g., electrosurgical device 100 can be delivered through a catheter sheath 170 to a treatment site). In some embodiments electrosurgical device 100 may not include, and may be used without, an exterior shaft 170, in which case proximal portions of electrodes 140 that extend proximally beyond proximal bolt circle 120 can be electrically insulated (e.g., coated with an insulating material).

Also, for example, in some embodiments electrosurgical device 100 can be used as a selectably monopolar or bipolar device, switchable between a bipolar mode and a monopolar mode. In the monopolar mode, at least one of electrodes 140 is connected to a power generator so as to deliver energy as a monopolar (active) electrode, and there is no return electrode on the device (rather, a ground pad on the patient may be used as known in the art). A monopolar electrode system can be particularly suitable for ablating tissue. In some embodiments, the monopolar electrode may be supplied with RF energy (including pulsed RF energy), ultrasonic energy, or any other suitable energy for ablating tissue.

Also, for example, in some embodiments of electrosurgical device 100 including more than one electrode 140, each electrode 140 can be similarly constructed (e.g., same material, shape, size), or one or more electrodes 140 can have different constructions from other electrode(s) 140 in the same electrosurgical device 100. In some embodiments, electrosurgical device 100 can include one or more electrodes similar to electrodes 140, but not configured to retain/release working fluid, and/or not having a lumen therethrough.

Figure 18:
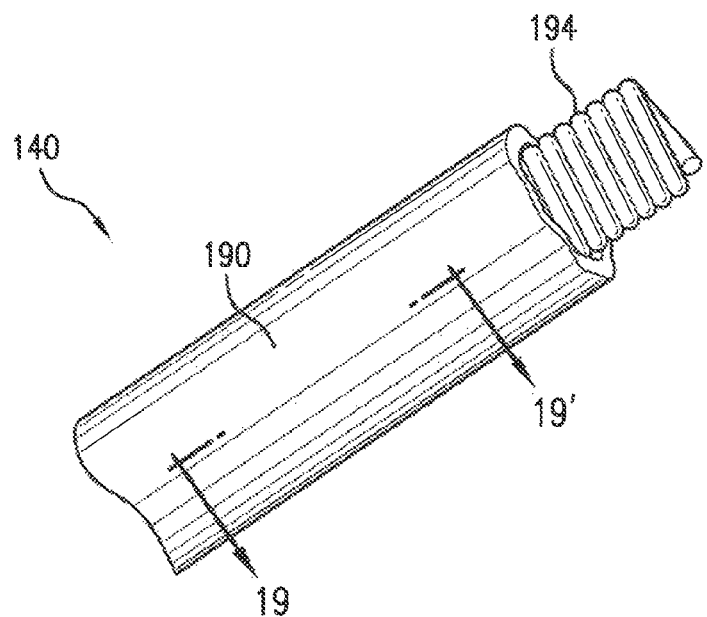
FIG. 18 illustrates a perspective view of a portion of an electrode according to an embodiment presented herein.
Figure 19:
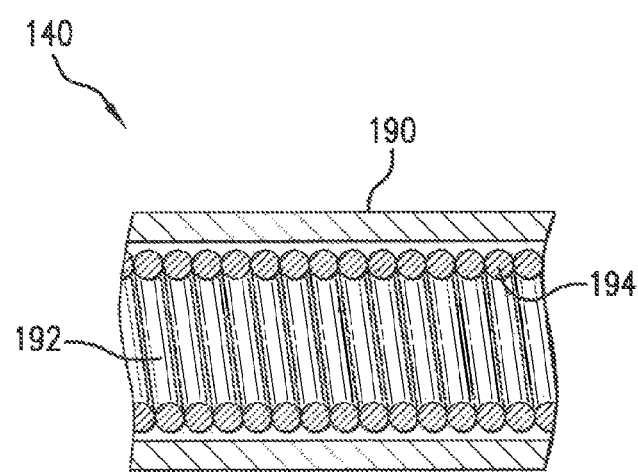
FIG. 19 illustrates a section view of a portion of the electrode of FIG. 18 along line 19-19', according to an embodiment presented herein.

Also, for example, in some embodiments, electrode 140 is formed of a non- or minimally-resilient material 190 where resilience of electrode 140 has been imparted (or augmented) by a spring internal to the non- or minimally-resilient material of electrode 140 (see FIGS. 18 and 19). For example, the non-resilient material 190 can form a hollow tube having a lumen 192, and an internal spring 194 can extend through lumen 192, augmenting non- or minimally-resilient material 190 with the inherent resilience of internal spring 194. In such embodiments, non- or minimally-resilient material 190 may include a helical discontinuity 144 as described herein, or may not include a helical discontinuity. In embodiments where non- or minimally-resilient material 190 does not include a helical discontinuity, working fluid may be retained/released by internal spring 194, as described herein, and non- or minimally-resilient material 190 may be configured to allow released fluid to pass therethrough (e.g., by weeping, via perforations, via incisions).

It should be apparent that adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

What is claimed is:

1. An electro surgical device, comprising:
a tubular shaft defining a shaft lumen; and
a tubular electrode defining an electrode lumen, the electrode being coupled to the shaft, wherein, in a straight configuration, the electrode is configured to retain fluid within the electrode lumen, and
wherein, in a bent configuration, the electrode is configured to release fluid from within the electrode lumen to an exterior of the electrode.

2. The device of claim 1, wherein the electrode is defined by an electrode wall having a spiral configuration.

3. The device of claim 1, wherein the electrode defines a laser-cut helical discontinuity along at least a portion of its length.

4. The device of claim 3, wherein the electrode is configured to release fluid in a bent configuration through spaces in the helical discontinuity.

5. The device of claim 1, wherein at least a portion of the electrode includes a coiled wire.

6. The device of claim 1, further comprising:
a second tubular electrode defining a second electrode lumen, the second electrode being coupled to the shaft,
wherein, in a straight configuration, the second electrode is configured to retain fluid within the second electrode lumen,
wherein, in a bent configuration, the second electrode is configured to release fluid from within the second electrode lumen to an exterior of the second electrode,
wherein the first electrode and the second electrode are configured to selectively release fluid independently of each other.

7. The device of claim 1, further comprising:
a second tubular electrode defining a second electrode lumen, the second electrode being coupled to the shaft,
wherein the first electrode and the second electrode are configured to be selectively energized independently of each other.

8. The device of claim 1, further comprising:
a second tubular electrode defining a second electrode lumen, the second electrode being coupled to the shaft; and
a balloon disposed about the shaft between the first and second electrodes and the shaft, wherein, in a straight configuration, the second electrode is configured to retain fluid within the second electrode lumen,
wherein, in a bent configuration, the second electrode is configured to release fluid from within the second electrode lumen to an exterior of the second electrode, and
wherein the first and second electrodes are configured to transition from the straight configuration to the bent configuration in response to inflation of the balloon.

9. The device of claim 8, wherein the extent that the first and second electrodes bend in response to inflation of the balloon is a function of the inflation amount of the balloon.

10. An electrosurgical device, comprising:
a tubular shaft defining a shaft lumen; and
a tubular electrode defining an electrode lumen, the electrode being coupled to the shaft, wherein, in a straight configuration, the electrode is configured to retain fluid within the electrode lumen, and wherein, in a bent configuration, the electrode is configured to release fluid from within the electrode lumen to an exterior of the electrode;

wherein the electrode is fixedly coupled to the shaft at the distal end of the electrode, wherein the electrode is slidably coupled to the shaft at a position proximal to the distal end of the electrode, wherein, in the straight configuration, the electrode is straight between its fixed coupling and its slidable coupling to the shaft, wherein, in the bent configuration, the electrode is bent between its fixed coupling and its slidable coupling to the shaft, and wherein, when transitioning between the straight configuration and the bent configuration, the electrode is configured to slide axially with respect to the shaft.

11. The device of claim 10, further including a bolt circle, and wherein the electrode is slidably coupled to the shaft by the bolt circle, and wherein the bolt circle is fixedly coupled to the shaft and defines a radial bore through which the electrode slidably extends.

12. The device of claim 10, further including a bolt circle, and wherein the electrode is slidably coupled to the shaft by the bolt circle, and; wherein the bolt circle is slidably coupled to the shaft and defines a radial bore through which the electrode fixedly extends.

* * * * *